US010224060B2

(12) United States Patent
Shinkai et al.

(10) Patent No.: US 10,224,060 B2
(45) Date of Patent: Mar. 5, 2019

(54) INTERACTIVE HOME-APPLIANCE SYSTEM, SERVER DEVICE, INTERACTIVE HOME APPLIANCE, METHOD FOR ALLOWING HOME-APPLIANCE SYSTEM TO INTERACT, AND NONVOLATILE COMPUTER-READABLE DATA RECORDING MEDIUM ENCODED WITH PROGRAM FOR ALLOWING COMPUTER TO IMPLEMENT THE METHOD

(71) Applicant: Sharp Kabushiki Kaisha, Sakai, Osaka (JP)

(72) Inventors: Makoto Shinkai, Sakai (JP); Toru Ueda, Sakai (JP); Hitoshi Hirose, Sakai (JP); Keisuke Iwasaki, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 81 days.

(21) Appl. No.: 15/120,944

(22) PCT Filed: Mar. 20, 2015

(86) PCT No.: PCT/JP2015/058452
§ 371 (c)(1),
(2) Date: Aug. 23, 2016

(87) PCT Pub. No.: WO2015/146824
PCT Pub. Date: Oct. 1, 2015

(65) Prior Publication Data

US 2016/0372138 A1 Dec. 22, 2016

(30) Foreign Application Priority Data

Mar. 25, 2014 (JP) ................................ 2014-062271

(51) Int. Cl.
*G10L 15/00* (2013.01)
*G10L 25/66* (2013.01)
(Continued)

(52) U.S. Cl.
CPC .............. *G10L 25/66* (2013.01); *A61B 5/165* (2013.01); *A61B 5/4803* (2013.01); *G10L 15/22* (2013.01);
(Continued)

(58) Field of Classification Search
CPC combination set(s) only.
See application file for complete search history.

(56) References Cited

U.S. PATENT DOCUMENTS

2003/0182117 A1 9/2003 Monchi et al.
2006/0100880 A1 * 5/2006 Yamamoto ............. G16H 50/20 704/270
(Continued)

FOREIGN PATENT DOCUMENTS

JP 2002-149706 A 5/2002
JP 2002-169804 A 6/2002
(Continued)

OTHER PUBLICATIONS

"Robot Kaden RX-V200 'Koekake Guide'", [online], 2013, 12, Sharp Corp., retrieved Apr. 7, 2015, <URL:http://www.sharp.co.jp/support/cocorobo/doc/rxv200_voiceguicle.pdf?productid=RX-V200>, 2 pages.

(Continued)

*Primary Examiner* — Vu B Hang
(74) *Attorney, Agent, or Firm* — Birch, Stewart, Kolasch & Birch, LLP

(57) ABSTRACT

A home-appliance system is provided that may alleviate user's stress or fatigue. The interactive home-appliance system includes an utterance unit, a voice input unit for
(Continued)

accepting input of a reply to voice, a storage unit for storing an assessment criterion for assessing stress or fatigue based on conversation with an utterer and data for outputting voice alleviating stress or fatigue, a determination unit for determining the utterer's stress or fatigue based on the assessment criterion and the reply, and a drive mechanism for performing an operation for assisting in the utterer's life. The utterance unit is configured to output an utterance based on the determination result and the data.

14 Claims, 16 Drawing Sheets

(51) Int. Cl.

| | |
|---|---|
| ***G10L 15/22*** | (2006.01) |
| ***A61B 5/16*** | (2006.01) |
| ***A61B 5/00*** | (2006.01) |
| ***G10L 17/22*** | (2013.01) |
| ***G10L 25/72*** | (2013.01) |
| *G10L 13/04* | (2013.01) |
| *G10L 15/26* | (2006.01) |
| *G10L 13/00* | (2006.01) |
| *G10L 15/08* | (2006.01) |
| *A61B 5/01* | (2006.01) |
| *A61B 5/08* | (2006.01) |
| *A61B 5/18* | (2006.01) |
| *G10L 25/63* | (2013.01) |

(52) U.S. Cl.

CPC .............. *G10L 17/22* (2013.01); *G10L 25/72* (2013.01); *A61B 5/002* (2013.01); *A61B 5/0022* (2013.01); *A61B 5/0077* (2013.01); *A61B 5/01* (2013.01); *A61B 5/0816* (2013.01); *A61B 5/18* (2013.01); *A61B 5/6887* (2013.01); *A61B 5/6893* (2013.01); *A61B 5/741* (2013.01); *A61B 5/7465* (2013.01); *A61B 2505/07* (2013.01); *G10L 13/00* (2013.01); *G10L 13/043* (2013.01); *G10L 15/265* (2013.01); *G10L 25/63* (2013.01); *G10L 2015/088* (2013.01)

(56) References Cited

U.S. PATENT DOCUMENTS

| | | | | |
|---|---|---|---|---|
| 2010/0049517 | A1* | 2/2010 | Huang | G06F 17/279 704/251 |
| 2010/0286490 | A1* | 11/2010 | Koverzin | G06F 19/3418 600/301 |
| 2013/0080169 | A1 | 3/2013 | Harada et al. | |

FOREIGN PATENT DOCUMENTS

| | | | |
|---|---|---|---|
| JP | 2003-058973 | A | 2/2003 |
| JP | 2003-108674 | A | 4/2003 |
| JP | 2003-228391 | A | 8/2003 |
| JP | 2004-240394 | A | 8/2004 |
| JP | 2005-258235 | A | 9/2005 |
| JP | 2006-338476 | A | 12/2006 |
| JP | 2008-269291 | A | 11/2008 |
| JP | 2009-032091 | A | 2/2009 |
| JP | 2010-073192 | A | 4/2010 |
| JP | 2010-157081 | A | 7/2010 |
| JP | 2013-072979 | A | 4/2013 |
| JP | 2013-109656 | A | 6/2013 |
| WO | WO 2004/027527 | A1 | 4/2004 |

OTHER PUBLICATIONS

Narimasu Kosei Hospital, "Checklist for Depression (SRQ-D (Self-Rating Questionnaire for Depression), Toho University Method)", retrieved Mar. 24, 2015, <URL:http://narimasukosei-hospital.jp/check/utsu/index.php>, 2 pages.

National Center of Neurology and Psychiatry, the cognitive behavioral therapy center, "What is cognitive behavior therapy", retrieved Mar. 24, 2015, <URL:http://www.ncnp.go.jp/cbt/about.html>, 2 pages.

National Institute for Health and Clinical Excellence, "Computerised cognitive behaviour therapy for depression and anxiety", Issued Feb. 2006, Information about NICE Technology Appraisal 97, pp. 1-9.

Sharp Corporation, "Voice Communication", 2015, <URL:http://www.sharp.co.jp/cocorobo/product/v200/>, 2 pages.

* cited by examiner

10
USER
11
USER
12
USER
FIRST UTTERANCE
SECOND UTTERANCE
REPLY
20
21
UTTERANCE UNIT
22
VOICE INPUT UNIT
24
STORAGE UNIT
25
DRIVE UNIT
23
DETERMINATION UNIT
27
CONTROL UNIT
26
COMMUNICATION UNIT
HOME-APPLIANCE SYSTEM
30
INFORMATION COMMUNICATION TERMINAL
40

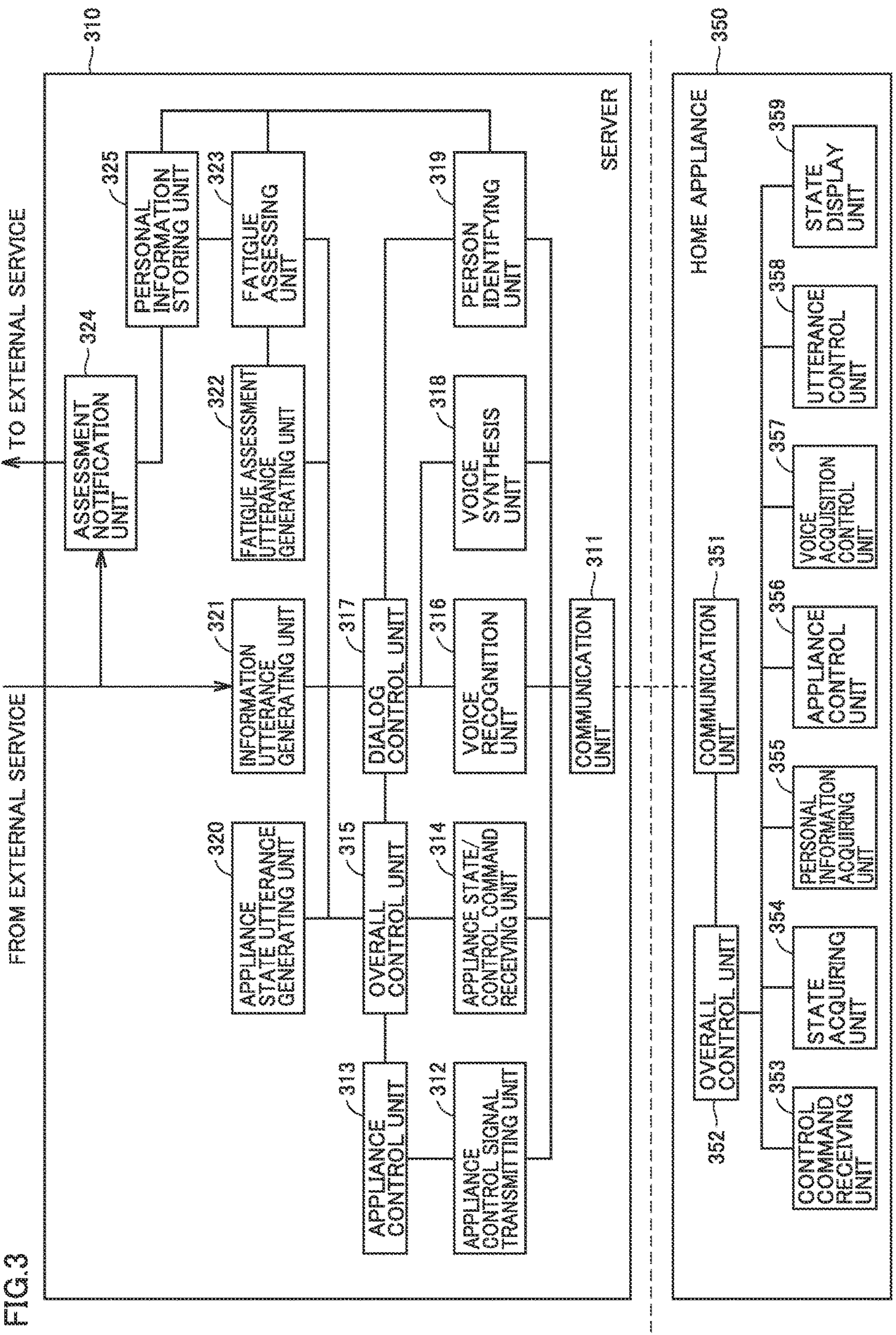
FIG.3
FROM EXTERNAL SERVICE
TO EXTERNAL SERVICE
310
SERVER
311 COMMUNICATION UNIT
312 APPLIANCE CONTROL SIGNAL TRANSMITTING UNIT
313 APPLIANCE CONTROL UNIT
314 APPLIANCE STATE/ CONTROL COMMAND RECEIVING UNIT
315 OVERALL CONTROL UNIT
316 VOICE RECOGNITION UNIT
317 DIALOG CONTROL UNIT
318 VOICE SYNTHESIS UNIT
319 PERSON IDENTIFYING UNIT
320 APPLIANCE STATE UTTERANCE GENERATING UNIT
321 INFORMATION UTTERANCE GENERATING UNIT
322 FATIGUE ASSESSMENT UTTERANCE GENERATING UNIT
323 FATIGUE ASSESSING UNIT
324 ASSESSMENT NOTIFICATION UNIT
325 PERSONAL INFORMATION STORING UNIT
350
HOME APPLIANCE
351 COMMUNICATION UNIT
352 OVERALL CONTROL UNIT
353 CONTROL COMMAND RECEIVING UNIT
354 STATE ACQUIRING UNIT
355 PERSONAL INFORMATION ACQUIRING UNIT
356 APPLIANCE CONTROL UNIT
357 VOICE ACQUISITION CONTROL UNIT
358 UTTERANCE CONTROL UNIT
359 STATE DISPLAY UNIT

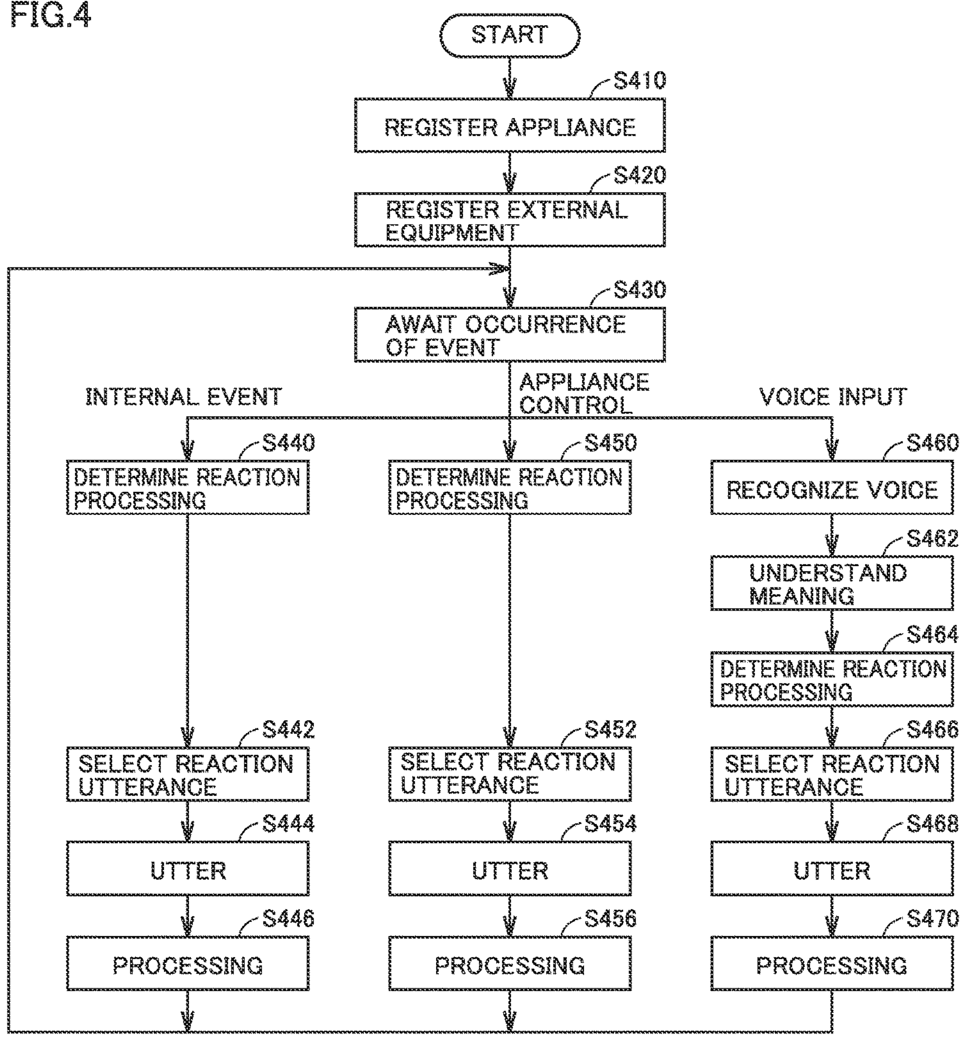
FIG.4
START
S410
REGISTER APPLIANCE
S420
REGISTER EXTERNAL EQUIPMENT
S430
AWAIT OCCURRENCE OF EVENT
INTERNAL EVENT
APPLIANCE CONTROL
VOICE INPUT
S440
DETERMINE REACTION PROCESSING
S450
DETERMINE REACTION PROCESSING
S460
RECOGNIZE VOICE
S462
UNDERSTAND MEANING
S464
DETERMINE REACTION PROCESSING
S442
SELECT REACTION UTTERANCE
S452
SELECT REACTION UTTERANCE
S466
SELECT REACTION UTTERANCE
S444
UTTER
S454
UTTER
S468
UTTER
S446
PROCESSING
S456
PROCESSING
S470
PROCESSING

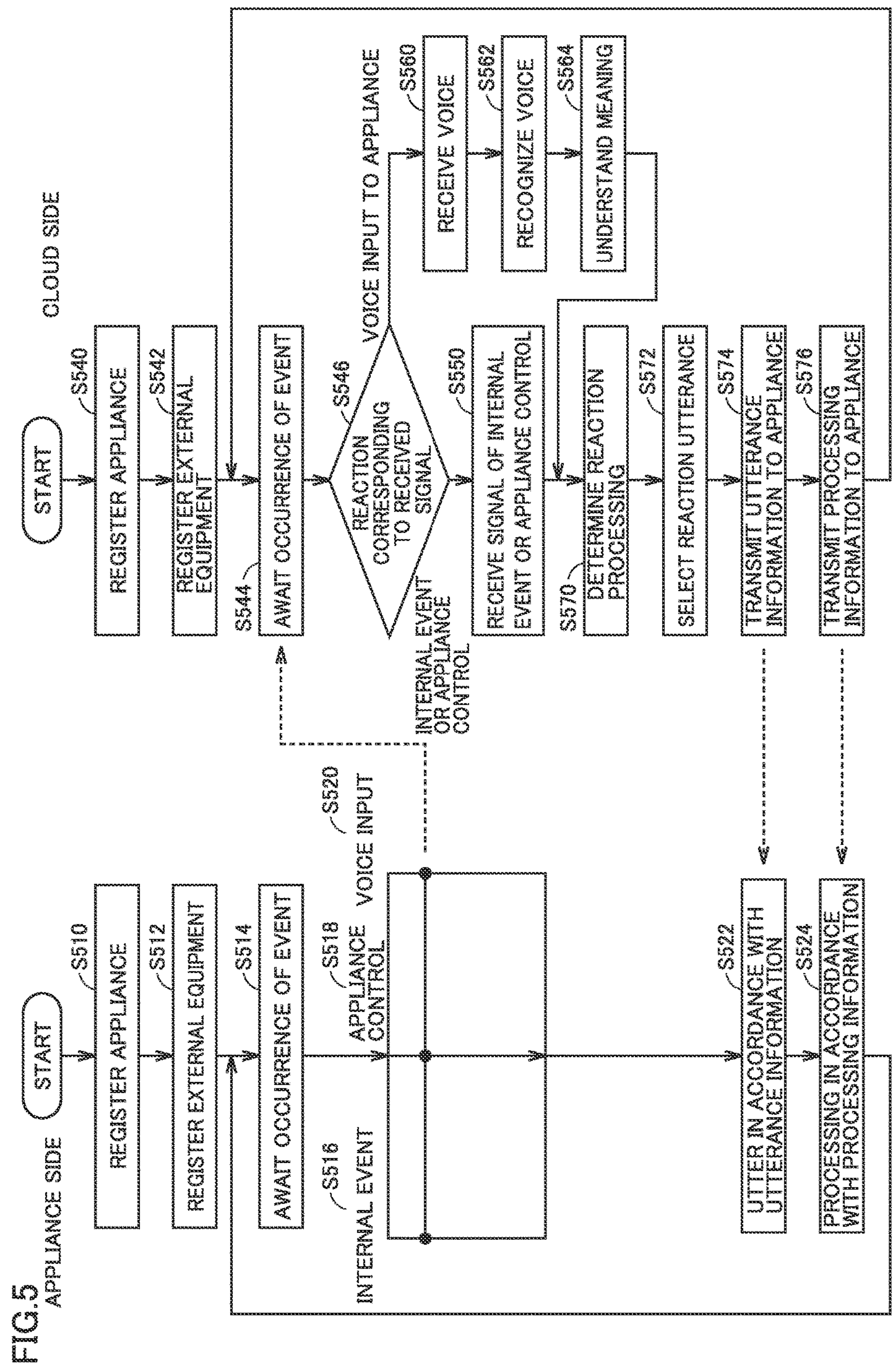
FIG.5
APPLIANCE SIDE
START
REGISTER APPLIANCE
S510
REGISTER EXTERNAL EQUIPMENT
S512
AWAIT OCCURRENCE OF EVENT
S514
S516
INTERNAL EVENT
S518
APPLIANCE CONTROL
S520
VOICE INPUT
UTTER IN ACCORDANCE WITH UTTERANCE INFORMATION
S522
PROCESSING IN ACCORDANCE WITH PROCESSING INFORMATION
S524
CLOUD SIDE
START
REGISTER APPLIANCE
S540
REGISTER EXTERNAL EQUIPMENT
S542
AWAIT OCCURRENCE OF EVENT
S544
REACTION CORRESPONDING TO RECEIVED SIGNAL
S546
VOICE INPUT TO APPLIANCE
INTERNAL EVENT OR APPLIANCE CONTROL
RECEIVE SIGNAL OF INTERNAL EVENT OR APPLIANCE CONTROL
S550
RECEIVE VOICE
S560
RECOGNIZE VOICE
S562
UNDERSTAND MEANING
S564
DETERMINE REACTION PROCESSING
S570
SELECT REACTION UTTERANCE
S572
TRANSMIT UTTERANCE INFORMATION TO APPLIANCE
S574
TRANSMIT PROCESSING INFORMATION TO APPLIANCE
S576

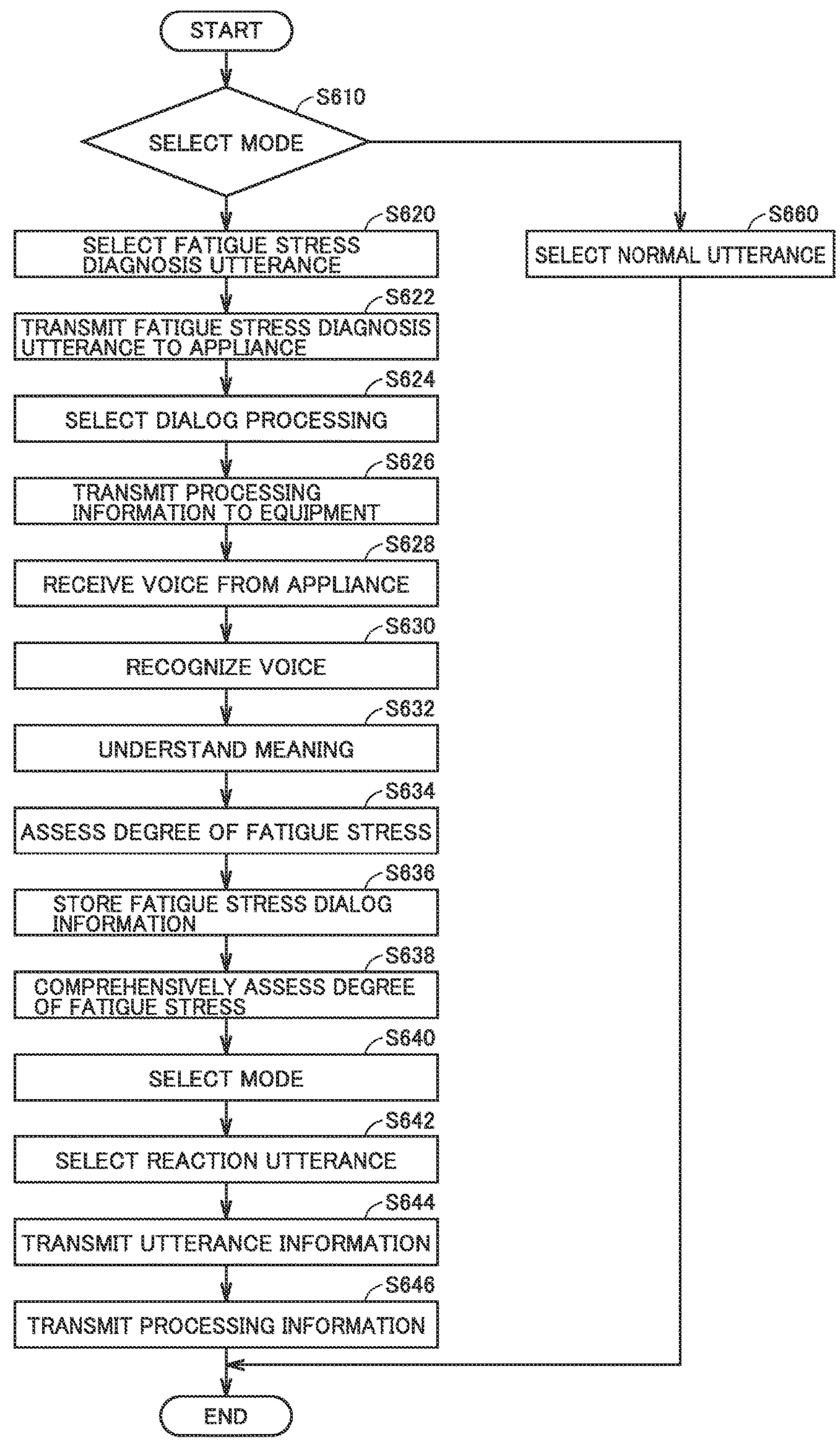
FIG.6
START
S610
SELECT MODE
S620
SELECT FATIGUE STRESS DIAGNOSIS UTTERANCE
S622
TRANSMIT FATIGUE STRESS DIAGNOSIS UTTERANCE TO APPLIANCE
S624
SELECT DIALOG PROCESSING
S626
TRANSMIT PROCESSING INFORMATION TO EQUIPMENT
S628
RECEIVE VOICE FROM APPLIANCE
S630
RECOGNIZE VOICE
S632
UNDERSTAND MEANING
S634
ASSESS DEGREE OF FATIGUE STRESS
S636
STORE FATIGUE STRESS DIALOG INFORMATION
S638
COMPREHENSIVELY ASSESS DEGREE OF FATIGUE STRESS
S640
SELECT MODE
S642
SELECT REACTION UTTERANCE
S644
TRANSMIT UTTERANCE INFORMATION
S646
TRANSMIT PROCESSING INFORMATION
S660
SELECT NORMAL UTTERANCE
END 700
MOUSE
2
KEYBOARD
3
RAM
4
CPU
1
HARD DISK
5
COMMUNICATION I/F
7
OPTICAL DISC DRIVE
6
MONITOR
8
9

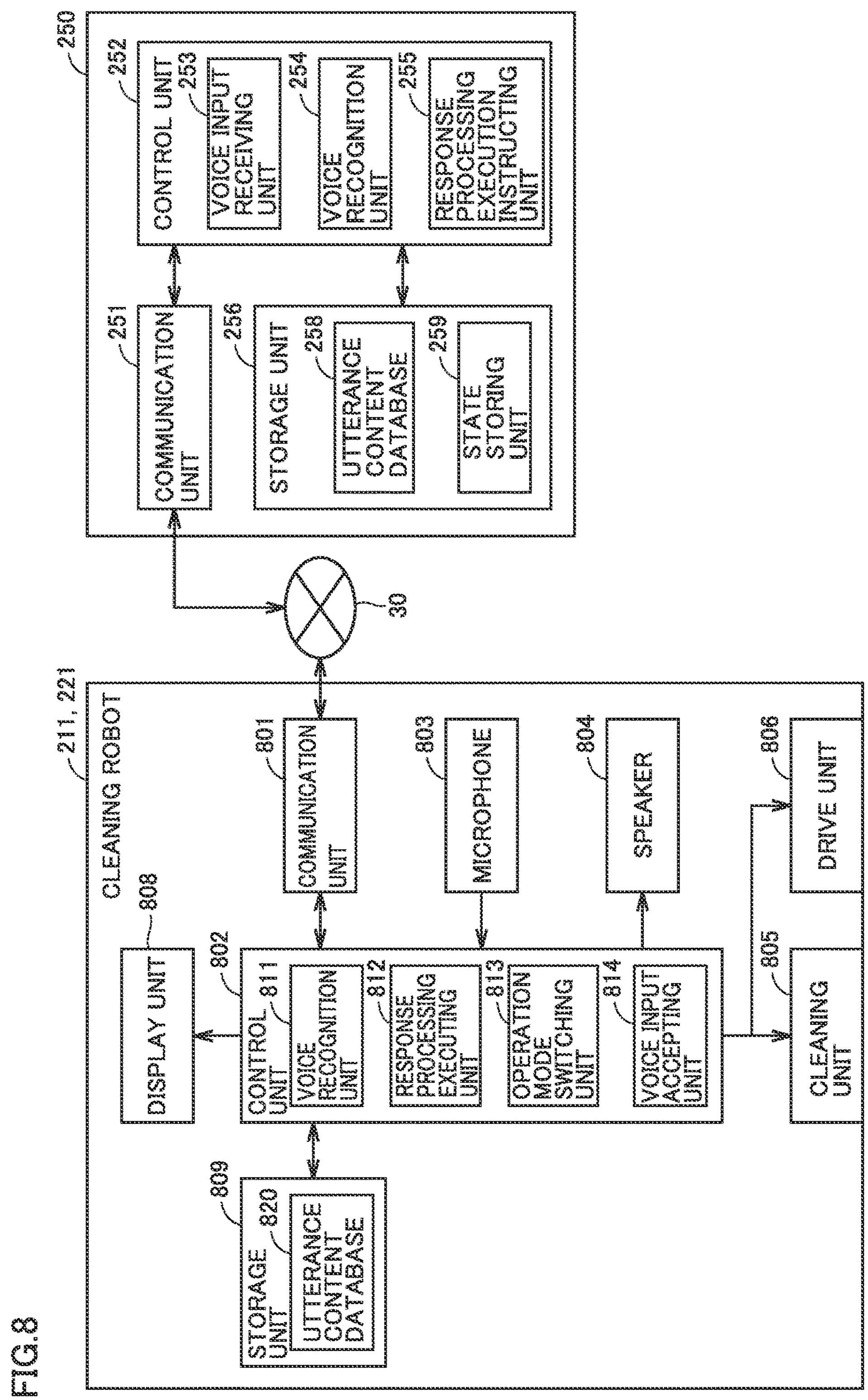
FIG.8
250
252
CONTROL UNIT
253
VOICE INPUT RECEIVING UNIT
254
VOICE RECOGNITION UNIT
255
RESPONSE PROCESSING EXECUTION INSTRUCTING UNIT
251
COMMUNICATION UNIT
256
STORAGE UNIT
258
UTTERANCE CONTENT DATABASE
259
STATE STORING UNIT
30
211, 221
CLEANING ROBOT
801
COMMUNICATION UNIT
803
MICROPHONE
804
SPEAKER
806
DRIVE UNIT
808
DISPLAY UNIT
802
CONTROL UNIT
811
VOICE RECOGNITION UNIT
812
RESPONSE PROCESSING EXECUTING UNIT
813
OPERATION MODE SWITCHING UNIT
814
VOICE INPUT ACCEPTING UNIT
805
CLEANING UNIT
809
STORAGE UNIT
820
UTTERANCE CONTENT DATABASE

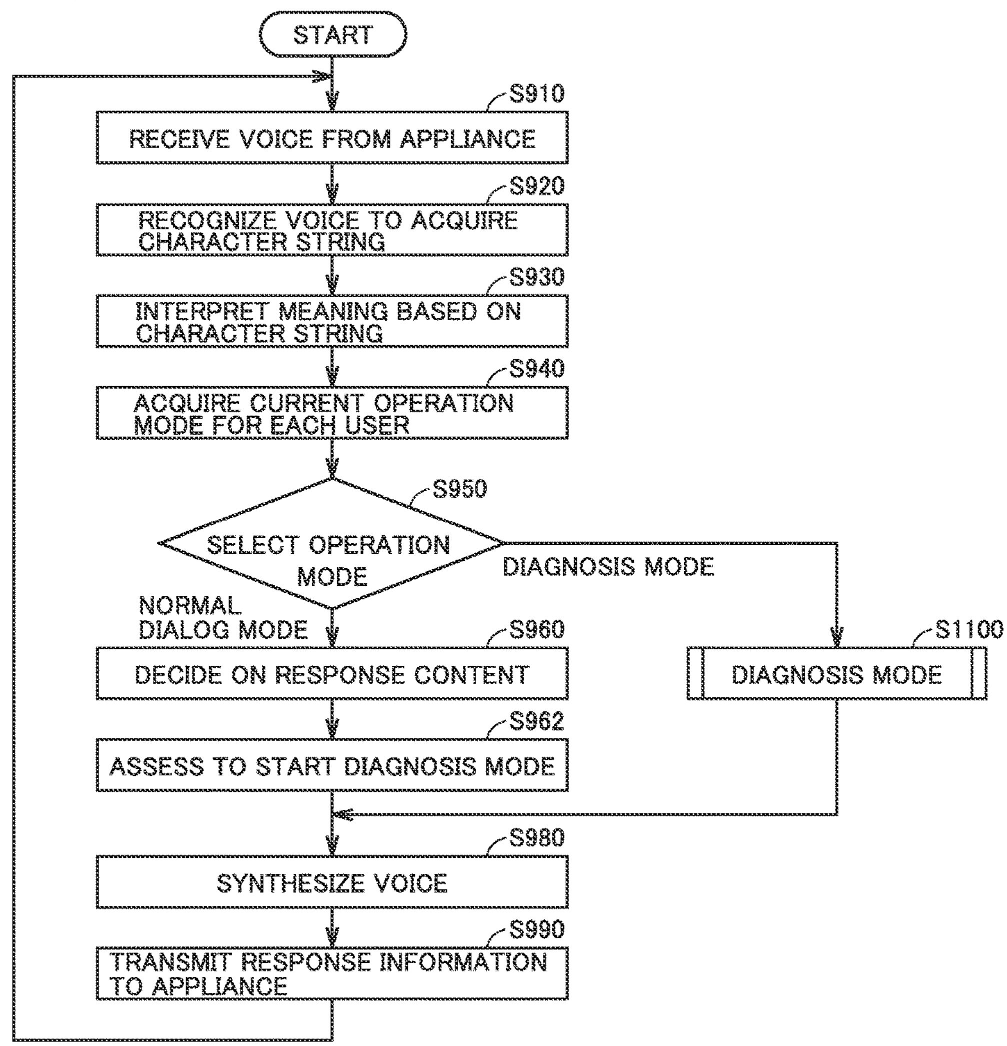
FIG.9
START
S910
RECEIVE VOICE FROM APPLIANCE
S920
RECOGNIZE VOICE TO ACQUIRE CHARACTER STRING
S930
INTERPRET MEANING BASED ON CHARACTER STRING
S940
ACQUIRE CURRENT OPERATION MODE FOR EACH USER
S950
SELECT OPERATION MODE
DIAGNOSIS MODE
NORMAL DIALOG MODE
S960
DECIDE ON RESPONSE CONTENT
S1100
DIAGNOSIS MODE
S962
ASSESS TO START DIAGNOSIS MODE
S980
SYNTHESIZE VOICE
S990
TRANSMIT RESPONSE INFORMATION TO APPLIANCE

| INPUT PHRASE ID (1001) | INPUT PHRASE (1002) |
| --- | --- |
| 1 | GOOD MORNING |
| 2 | HELLO |
| 3 | FINE |
| 4 | GREAT |
| 5 | I'M TIRED |
| 6 | I FEEL SLUGGISH |
| ... | ... |

1010

| RESPONSE ID (1011) | INPUT PHRASE ID (1012) | UTTERANCE MESSAGE (1013) | OPERATION PATTERN (1014) |
| --- | --- | --- | --- |
| 1 | 1 | GOOD MORNING ! HAVE A NICE DAY ! | PATTERN A |
| 2 | 1 | GOOD MORNING | PATTERN B |
| 3 | 1 | AH, I'M STILL SLEEPY | PATTERN C |
| 4 | 3 | I'M DOING WELL | PATTERN A |
| 5 | 4 | DON'T WORK TOO HARD | PATTERN A |
| 6 | 5 | HI ! WHY NOT GET SOME REST ? | PATTERN B |
| 7 | 6 | HI ! WHY NOT GET SOME REST ? | PATTERN B |
| ... | ... | ... | ... |

| DIAGNOSIS ID (1211) | DIAGNOSIS MESSAGE (1212) | TERMS OF VALIDITY (DAYS) (1213) |
|---|---|---|
| 1 | HOW ARE YOU TODAY? | 1 |
| 2 | DID YOU SLEEP WELL LAST NIGHT? | 1 |
| 3 | DO YOU SLEEP BADLY LATELY? | 7 |
| 4 | DO YOU HAVE APPETITE? | 7 |
| 5 | HAVE YOU HAD SUDDEN DIFFICULTY TO BREATHE LATELY? | 7 |
| 6 | DO YOU FEEL SLUGGISH LATELY? | 7 |
| 7 | HAVE YOU BEEN BUSY AT WORK? | 7 |
| ... | ... | ... |

1220

| USER ID (1221) | INPUT DATE AND TIME (1222) | DIAGNOSIS ID (1223) | UTTERANCE MESSAGE (1224) | INPUT PHRASE (1225) | EVALUATION (1226) |
|---|---|---|---|---|---|
| ... | ... | | ... | | |
| 1010 | 2014-02-20 06:33:20 | 1 | HOW ARE YOU TODAY? | I'M A LITTLE BIT TIRED | −1 |
| 1010 | 2014-02-20 06:33:56 | 2 | I SEE, DID YOU SLEEP WELL LAST NIGHT? | I SLEPT WELL | +1 |
| 1010 | 2014-02-20 06:34:32 | 7 | | WELL, I'M BUSY THIS WEEK | −1 |
| 829 | 2014-02-20 10:45:54 | null | | AH, I'M TIRED | +1 |
| ... | ... | ... | ... | ... | ... |

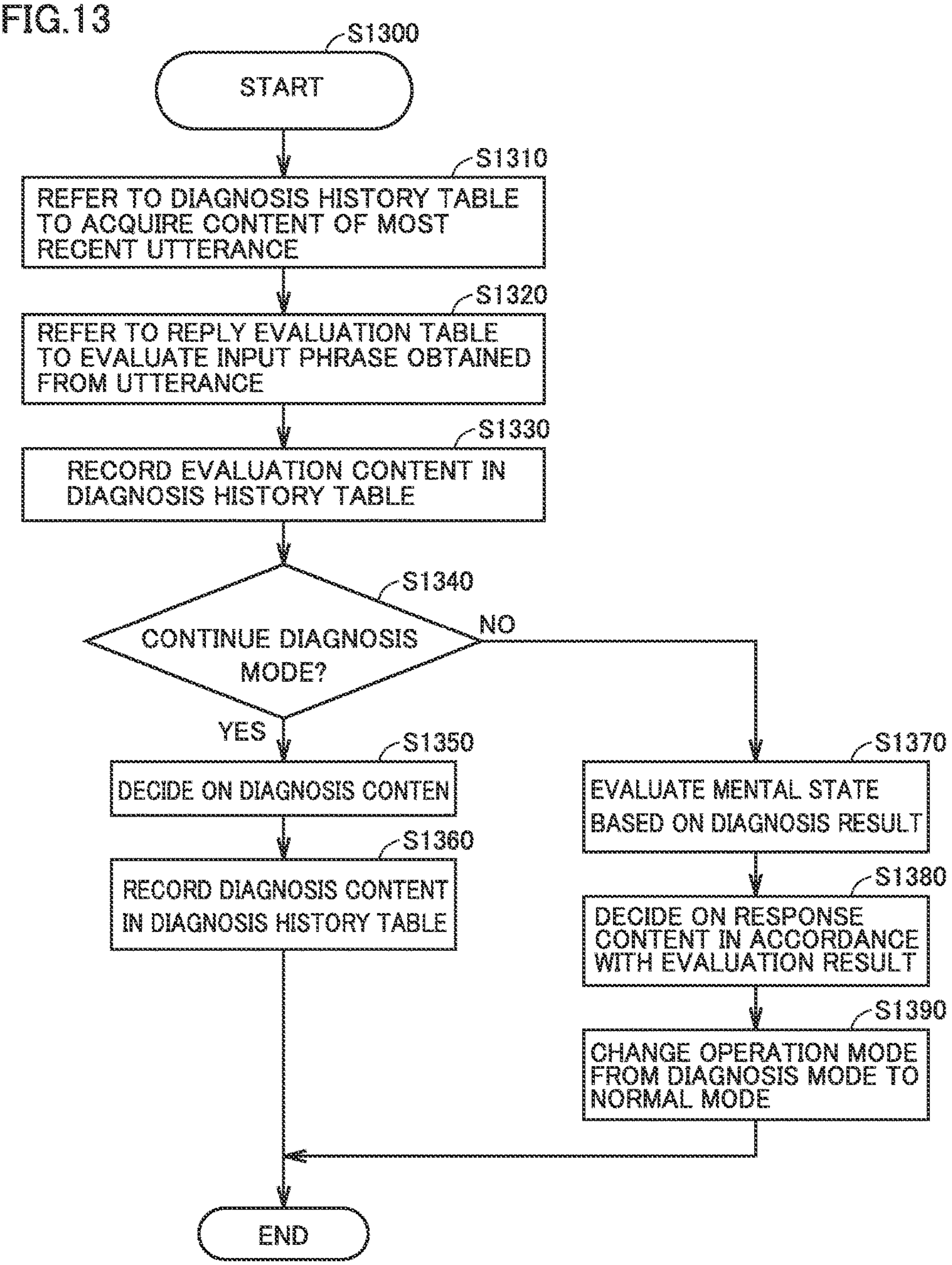
FIG.13
S1300
START
S1310
REFER TO DIAGNOSIS HISTORY TABLE TO ACQUIRE CONTENT OF MOST RECENT UTTERANCE
S1320
REFER TO REPLY EVALUATION TABLE TO EVALUATE INPUT PHRASE OBTAINED FROM UTTERANCE
S1330
RECORD EVALUATION CONTENT IN DIAGNOSIS HISTORY TABLE
S1340
CONTINUE DIAGNOSIS MODE?
NO
YES
S1350
DECIDE ON DIAGNOSIS CONTEN
S1360
RECORD DIAGNOSIS CONTENT IN DIAGNOSIS HISTORY TABLE
S1370
EVALUATE MENTAL STATE BASED ON DIAGNOSIS RESULT
S1380
DECIDE ON RESPONSE CONTENT IN ACCORDANCE WITH EVALUATION RESULT
S1390
CHANGE OPERATION MODE FROM DIAGNOSIS MODE TO NORMAL MODE
END

| REPLY ID | DIAGNOSIS ID | INPUT PHRASE | EVALUATION |
|---|---|---|---|
| 1 | 1 | DOING WELL | +1 |
| 2 | 1 | GREAT | +2 |
| 3 | 1 | NOT GOOD | −1 |
| 4 | 1 | TIRED | −1 |
| 5 | 1 | SLUGGISH | −1 |
| 6 | 1 | SLEEPY | −1 |
| 7 | 2 | YES | +1 |
| 8 | 2 | SLEPT WELL | +1 |
| 9 | 2 | NOT SO GOOD | −1 |
| 10 | 2 | DIDN'T SLEEP | −1 |
| 11 | 3 | YES | −1 |
| 12 | 3 | FEEL SO | −1 |
| 13 | 3 | DON'T FEEL SO | +1 |
| 14 | 3 | NO | +1 |
| ... | ... | ... | ... |

| MESSAGE ID | MESSAGE |
|---|---|
| 1 | TELL ME ABOUT IT LATER |
| 2 | TELL ME IF YOU HAVE ANY PROBLEM |
| 3 | TAKE CARE OF YOURSELF |
| ... | ... |

1520

1521 1522

| MESSAGE ID | MESSAGE |
|---|---|
| 1 | ARE YOU A LITTLE BIT TIRED? WHY NOT GET SOME REST TODAY |
| 2 | ARE YOU A LITTLE BIT TIRED? TAKE IT EASY |
| 3 | YOU ARE DOING WELL |
| 4 | DON'T WORK TOO HARD |
| 5 | I'M WORRYING ABOUT YOU |
| 6 | WHY DON'T YOU GO TO BED EARLY? |
| 7 | WHY DON'T YOU TAKE DAY OFF TOMORROW? |
| 8 | I'M WORRYING ABOUT YOU |
| 9 | YOU HAVE A BASEBALL GAME IN TOWN TOMORROW |
| 10 | FUTON GA FUTTONDA |
| ... | ... |

1530

VOICE CONTENT

FIG.16
(A)
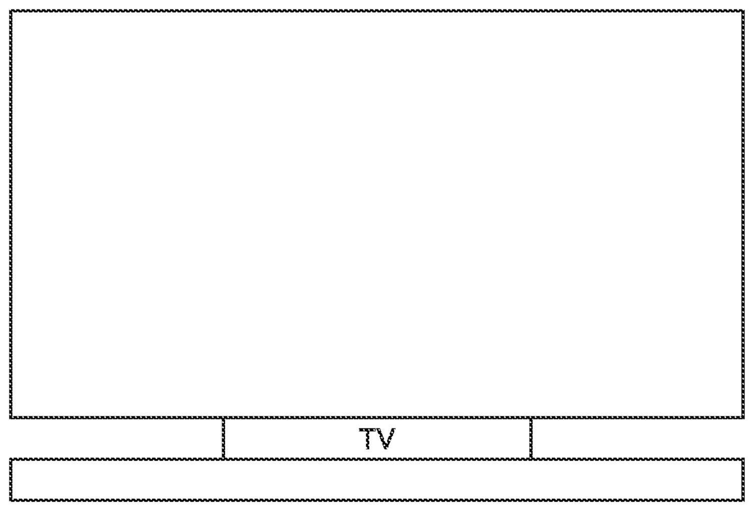
(B)
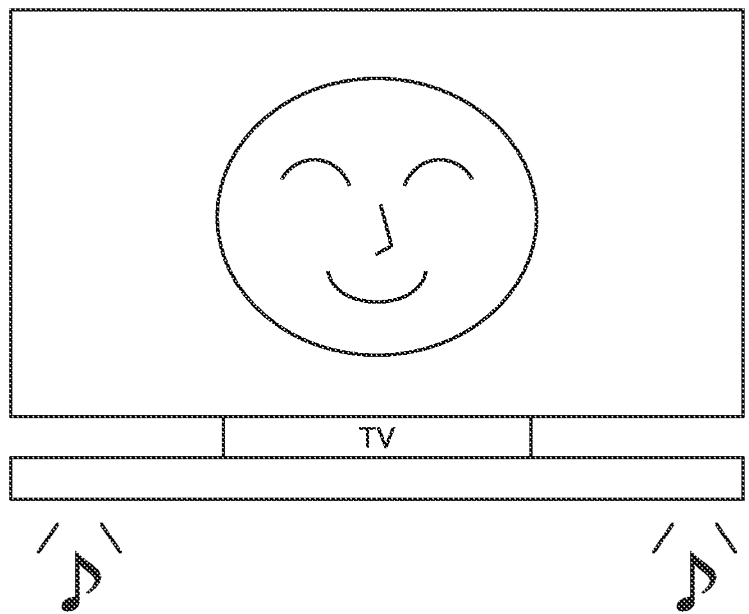

INTERACTIVE HOME-APPLIANCE SYSTEM, SERVER DEVICE, INTERACTIVE HOME APPLIANCE, METHOD FOR ALLOWING HOME-APPLIANCE SYSTEM TO INTERACT, AND NONVOLATILE COMPUTER-READABLE DATA RECORDING MEDIUM ENCODED WITH PROGRAM FOR ALLOWING COMPUTER TO IMPLEMENT THE METHOD

TECHNICAL FIELD

The present disclosure relates to a home appliance capable of voice recognition, and more particularly to an interactive home appliance.

BACKGROUND ART

Cognitive behavioral therapy is known as one of techniques for alleviating stress or mental fatigue and improving mental disorders such as depression. Cognitive behavioral therapy is defined as "a kind of mental therapy (psychological therapy) which works on cognition to make people feel better" (see, for example, NPD 1). This cognitive behavioral therapy is an approach that does not rely on physical or chemical means but improves symptoms through enlightenment and dialogs mainly based on languages.

In Britain, National Institute for Health and Clinical Excellence provides a guidance for computer-assisted cognitive behavioral therapy, entitled "Computerised cognitive behaviour therapy for depression and anxiety", http://publications.nice.org.uk/computerised-cognitive-behaviour-therapy-for-depression-and-anxiety-ta97/guidance, in which its effects are also described.

Beating the Blues (http://www.beatingtheblues.co.uk/) in Britain provides on-line cognitive behavioral therapy actually using computers, and its effects is also described in the guideline above.

On the other hand, in Japan, for example, the SRQ-D check sheet developed by Toho University is utilized in local governments and hospitals as an easy screening for mild depression, which only requires users to answer a simple questionnaire (see, for example, PTD 2). This is to easily diagnose suspicion of depression by allowing users to select an answer from four choices "No", "Sometimes", "Often", and "Always" for 18 questions including, for example, Q1: Do you feel sluggish and get easily tired? and Q2: Are you nervous about noise?

As described above, it is known that an easy diagnosis is made through a simple linguistic questionnaire, and symptoms are alleviated through online dialogs using computers.

In this regard, Japanese Patent Laying-Open No. 2003-108674 (PTD 1) discloses a system for conducting counseling using a personal computer. Japanese Patent Laying-Open No. 2013-109656 (PTD 2) discloses an apparatus that does not require a user to take a test consciously, but determines that the user undergoes stress based on text input to a computer usually used by the user.

On the other hand, apart from alleviation of stress or fatigue, for example, there are home appliances that communicate via voice. For example, the robot vacuum cleaner (RX-V200) sold by Sharp Corporation is equipped with a function of performing voice recognition and voice synthesis to have conversations with users (NPD 3).

CITATION LIST

Patent Document

PTD 1: Japanese Patent Laying-Open No. 2003-108674
PTD 2: Japanese Patent Laying-Open No. 2013-109656

Non Patent Document

NPD 1: National Center of Neurology and Psychiatry, the cognitive behavioral therapy center, website (http://www.ncnp.go.jp/cbt/about.html)
NPD 2: Narimasu Kosei Hospital, website (http://narimasu-kosei-hospital.jp/check/utsu/index.php)
NPD 3: Sharp Corporation, website (http://www.sharp.co.jp/cocorobo/product/v200/)

SUMMARY OF INVENTION

Technical Problem

An experiment was conducted with robot vacuum cleaners equipped with the function of performing appliance control (for example, starting and stopping cleaning) and conversations (for example, weather forecast, menu proposals, and greetings) through voice recognition. Specifically, an experiment was conducted, in which 12 subjects used the robot vacuum cleaners for two months. According to the case result, it has been found that the conversations for controlling cleaning functions (utterances of the subjects who are the users) take up 20% or less of the entire utterances with the robot vacuum cleaner, and most of the utterances are utterances in which the subjects reveal their feelings and states, utterances for asking about weather and other information, utterances for acquiring knowledge of geography and names of animals and plants, utterances for giving feedbacks such as "Like" to the contents posted on social network services to show sympathy for the contents, greetings to the robot vacuum cleaners, utterances for riddles and other games, and the like.

That is, it is understood that when a device (in other words, home appliance) having a function of supporting activities in daily life (hereinafter called housework) is given an instruction to carry out the function using linguistic information, the device is naturally allowed to carry out other greetings, acquisition of weather forecast and other information, and emotional dialogs (for example, tired, enjoy), in addition to the instruction.

On the other hand, although there is a growing number of people who need mental support due to changes in social environments or other reasons, the supply of people who can provide support has not caught up. Thus, there is a need for techniques for providing mental support.

The present disclosure is made in order to solve the aforementioned problems. An object in an aspect is to provide an interactive home-appliance system or an interactive home appliance in which a device having a function of supporting housework has a function of being instructed via linguistic information and also provides support for alleviating users' fatigue, stress, and other mental burdens through linguistic information. An object in another aspect is to provide a server device for providing support for alleviating users' fatigue, stress, and other mental burdens through linguistic information.

An object in another aspect is to provide a method for allowing a device having a function of supporting housework to accept an instruction via linguistic information while providing support for alleviating users' fatigue, stress, and other mental burdens through linguistic information. An object in yet another aspect is to provide a program for allowing a computer to execute the method.

Solution to Problem

An interactive home-appliance system according to an embodiment includes a voice output unit for outputting voice, a voice input unit configured to accept input of voice, an assessment criterion storing unit configured to store an assessment criterion for assessing stress or fatigue based on conversation with an utterer, a dialog data storing unit configured to store data for outputting voice alleviating stress or fatigue, and a determination unit configured to determine stress or fatigue of an utterer, based on the assessment criterion and a response of the utterer to voice output from the interactive home-appliance system. The voice output unit is configured to output an utterance based on a result of the determination and the data.

In an example according to an aspect, the user interacts with the home appliance, whereby the user's fatigue or stress may be alleviated.

The foregoing and other objects, features, aspects and advantages of the present invention will become more apparent from the following detailed description of the present invention when taken in conjunction with the accompanying drawings.

BRIEF DESCRIPTION OF DRAWINGS

FIG. 3 is a block diagram illustrating a detailed configuration of a server and a home appliance included in home-appliance system 20.

FIG. 4 is a flowchart illustrating part of the processing in home-appliance system 20.

FIG. 5 is a flowchart illustrating part of the processing executed by home appliance 350 and server 310 included in home-appliance system 20.

FIG. 6 is a flowchart illustrating part of the processing executed by server 310 to understand the meaning of an utterance to home appliance 350 in home-appliance system 20.

FIG. 8 is a block diagram illustrating a hardware configuration of cleaning robots 211, 221.

FIG. 9 is a flowchart illustrating exemplary voice recognition processing executed by computer 700 functioning as server 310.

FIG. 10 is a diagram illustrating an embodiment of the structure of a database in server 310.

FIG. 12 is a diagram conceptually illustrating an embodiment of storage of data for diagnosis in hard disk 5.

FIG. 13 is a flowchart illustrating an example of the diagnosis mode processing executed by CPU 1.

FIG. 14 is a diagram conceptually illustrating an embodiment of storage of data in hard disk 5.

FIG. 15 is a diagram conceptually illustrating an embodiment of storage of data in hard disk 5.

FIG. 16 is a diagram illustrating an aspect in which television 215 interacts with a user.

DESCRIPTION OF EMBODIMENTS

Embodiments of the present invention will be described below with reference to the drawings. In the following description, the same components are denoted with the same reference signs. Their names and functions are also the same. Therefore, a detailed description thereof will not be repeated.

[Technical Concept]

Figure 1:
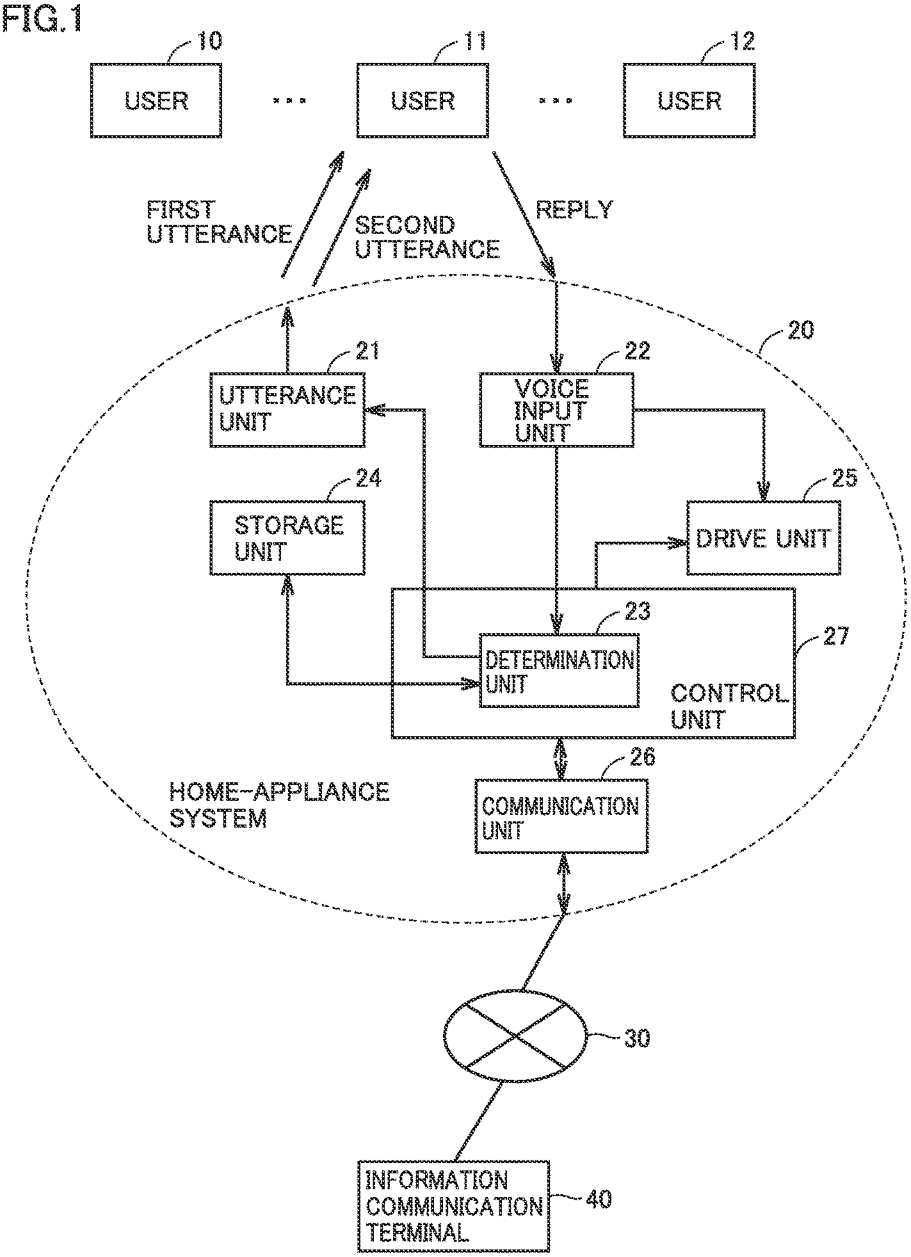
FIG. 1 is a diagram illustrating a configuration of interactive home-appliance system 20 according to the present embodiment.

Referring to FIG. 1, the technical concept according to the present embodiment will be described. FIG. 1 is a diagram illustrating the configuration of an interactive home-appliance system 20 according to the present embodiment. Home-appliance system 20 includes an utterance unit 21, a voice input unit 22, a storage unit 24, a drive mechanism 25, and a communication unit 26. Control unit 27 includes a determination unit 23. Control unit home-appliance system 20 can interact with, for example, one or more users 10, 11, 12.

In the following description, home-appliance system 20 may be implemented by appliances that provide daily support. In an aspect, the appliances may include household electrical and mechanical instruments for private use, generally called "home appliances", and office appliances for business use. Home appliances may include, for example, vacuum cleaners, refrigerators, air conditioning equipment (hereinafter also called "air conditioners"), televisions, lights, sphygmomanometers, electric rice cookers, electromagnetic cookers, sinks, weight scales, home planetariums, and other instruments.

The appliances in the present embodiment are not limited to those for indoor use but may include those for outdoor use such as automobiles, bicycles, motorcycles, and electrically driven chairs. The office appliances may include, for example, instruments used by business operators, such as copiers, facsimile machines, paper shredders, teleconference systems, and video conferences.

In an aspect, for example, home-appliance system 20 outputs voice through utterance unit 21 (first utterance). User 11 replies in response to the voice. Voice input unit 22 accepts input of the reply by user 11.

Voice input unit 22 converts the reply into a voice signal. Communication unit 26 can connect to the Internet 30 to communicate with an information communication terminal 40. The communication is not limited to any particular mode. Control unit 27 controls the operation of home-appliance system 20. In control unit 27, determination unit 23 determines the psychological state of user 11 based on the signal and data stored in storage unit 24. This determination is made based on, for example, data stored in storage unit 24 in advance. In another aspect, determination unit 23 may connect to the Internet 30 through communication unit 26 to communicate with information communication terminal 40, and information communication terminal 40 may make the determination.

Determination unit 23 transmits a signal based on the result of the determination to utterance unit 21. Utterance unit 21 outputs voice based on the signal (second utterance). Listening to the voice (second utterance) output by home-appliance system 20, user 11 may ease the psychological state with its content.

In an aspect, home-appliance system 20 may be implemented as one or more home appliances. In another aspect, home-appliance system 20 may be implemented by a home appliance and a server that can communicate with the home appliance.

Users 10, 11, 12 are identified by, for example, manipulation of dedicated switches allocated to the users, face images, fingerprints, voice prints, or other biological information. The accuracy of identification may not be 100% and may be such a degree, for example, that can identify who is the user in the family of four. On the other hand, in another aspect, an authentication technique that requires 100% accuracy may be used. For example, in hospitals and other medical facilities with a number of inpatients, or in welfare facilities with a number of residents, the 100% authentication technique may be used. Alternatively, in yet another aspect, the accuracy of identification may be variable.

As data used for determining the user's mental state, for example, the contents of conversation with a home appliance (voice recognition result), voice (the result of voice frequency analysis), the captured face image of the user, the amount of perspiration of the user, the user's body temperature, the user's breathing, and the like may be used. As for the conversation, the mental state may be estimated from the content of a reply. As for the face image, for example, if the user's face turns red, it may be estimated that the user is in excitement. As for the amount of perspiration, if the amount exceeds a predefined amount, it may be estimated that the user is in excitement. As for the breathing, if the user's breathing becomes faster than the normal respiratory rate, it may be estimated that the user is in excitement.

Alternatively, as yet another embodiment, the user's mental state may be estimated from the tone of the user's voice. For example, if the tone of the voice is lower than usual, it may be estimated that the user is more tired than in the normal state. Conversely, if the tone of the voice is higher than usual, it may be determined that the user is in excitement.

[Usage of Home-Appliance System]

Figure 2:
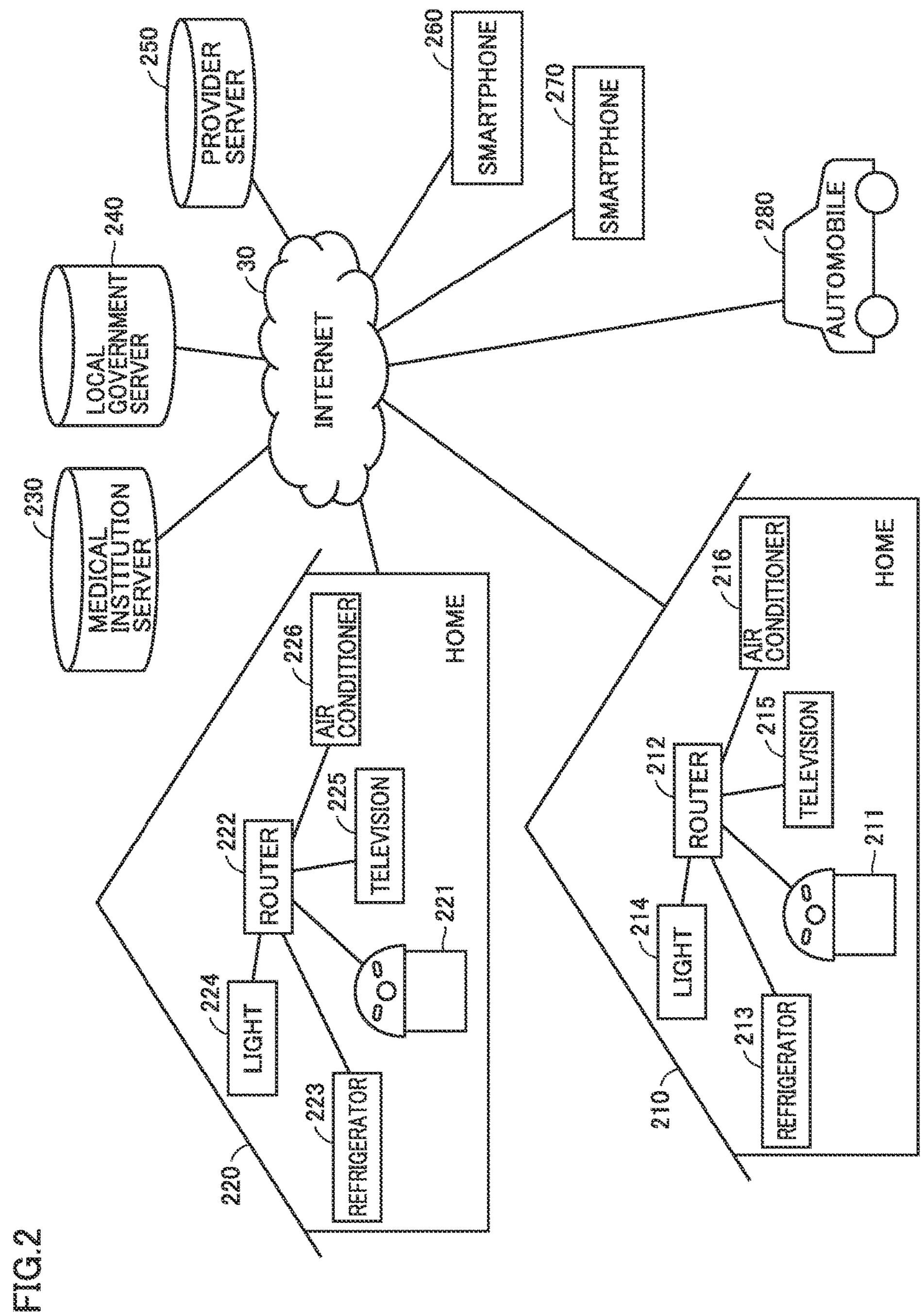
FIG. 2 is a diagram illustrating an aspect in which interactive home-appliance system 20 is used.

Referring to FIG. 2, the technical concept according to the present embodiment will be further described. FIG. 2 is a diagram illustrating an aspect in which interactive home-appliance system 20 is used. In an aspect, home-appliance system 20 is implemented as cleaning robots 211, 221, which are an embodiment of the home appliance.

At the user's own home 210, cleaning robot 211 is connected to be able to communicate with each of a refrigerator 213, a light 214, a television 215, and an air conditioner 216 through a router 212. Refrigerator 213, light 214, television 215, and air conditioner 216 each have a network function and execute a unique operation based on a signal sent from cleaning robot 211. Examples of the unique operation may include the processing of displaying the contents of refrigerator 213, the processing of adjusting the luminance of light 214, the processing of adjusting channels and volume of television 215, and temperature control of air conditioner 216.

Home 210 is connected to the Internet 30. To the Internet 30, someone else's home 220, a medical institution server 230, a local government server 240, a provider server 250, smartphones 260, 270, and an automobile 280 are further connected to be able to communicate.

Someone else's home 220 is, for example, the house of a relative of the resident of home 210. Cleaning robot 221 is present in home 220. Cleaning robot 221 is connected to be able to communicate with each of a refrigerator 223, a light 224, a television 225, and an air conditioner 226 through a router 222. Refrigerator 223, light 224, television 225, and air conditioner 226 have the similar functions as refrigerator 213, light 214, television 215, and air conditioner 216, respectively. Therefore, a detailed description thereof will not be repeated.

Medical institution server 230 is used, for example, by a hospital or other medical institutions that the user himself/herself or his/her relative visits. Local government server 240 is used by the local government of the residence of the user himself/herself or his/her relative. Provider server 250 is operated and used by an information provider for transmitting information to each of cleaning robots 211, 221. Medical institution server 230, local government server 240, and provider server 250 are each implemented, for example, by a computer device having a well-known configuration.

Smartphones 260, 270 are used as information processing communication terminals by members of a provider that provides the user's family or the user himself/herself with medical service. The information processing communication terminals are not limited to smartphones, and tablet terminals, PDAs (Personal Digital Assistants), or other terminals may be used by the family or the members of the provider. The configuration of smartphones 260, 270 is easily understood by those skilled in the art. Therefore, a description of the configuration will not be repeated.

Automobile 280 has a network communication function and may be controlled by cleaning robots 211, 221 and other equipment having the communication function.

SCENARIO EXAMPLES

Possible scenarios in the present embodiment will be described below. In each of the following scenarios, cleaning robot 211 is used as an example of home appliances. However, the applicable range of the technical concept according to the present embodiment is not limited to cleaning robot 211. The technical concept is applicable to appliances at least having the voice recognition function and the information processing function, for example, refrigerator 213, light 214, television 215, air conditioner 216, automobile 280, and other appliances.

(Scenario 1) <First Embodiment>

As a first embodiment, a home appliance having an interactive function may give an utterance to care about the user based on conversation from a user. For example, the user comes back home 210. The user utters "I'm back." Cleaning robot 211 recognizes the utterance and then detects that the user is a user already registered in cleaning robot 211, based on voice information registered in advance. Cleaning robot 211 outputs a reply "Welcome back" held as information prepared in advance. Subsequently, if the user says "Clean up," cleaning robot 211 replies "OK" and starts executing the cleaning function. Cleaning robot 211 runs under a predefined program and cleans the living room and other rooms.

When a predetermined condition is established, cleaning robot 211 asks "You've been tired, haven't you?" Here, examples of the predetermined condition may include the elapse of a predefined time since the user's last utterance, detecting that the user who has had a dialog with cleaning robot 211 is a user registered in advance, and the like. In another aspect, a question may be uttered at random, based on random numbers produced in cleaning robot 211.

In response to the question, the user replies to cleaning robot 211, "Yeah, I've been busy at work." Cleaning robot 211 recognizes the reply and then diagnoses the user in the inside of cleaning robot 211 to obtain a diagnosis result. Alternatively, in another aspect, cleaning robot 211 transmits a voice signal of the reply to provider server 250 connected to the Internet 30. Provider server 250 makes a diagnosis based on the voice signal and returns the diagnosis result to cleaning robot 211.

Cleaning robot 211 acquires the diagnosis result and then utters "Take it easy." In response to the utterance, the user replies "Sure. Thanks." Cleaning robot 211 recognizes the reply and then replies "Not at all."

Through such a dialog, the user recognizes that he/she is cared about by cleaning robot 211, and then the user's fatigue or stress may be alleviated.

(Scenario 2) <Second Embodiment>

As a second embodiment, cleaning robot 211 may give an utterance to care about the user by referring to history of dialog with the user.

Cleaning robot 211 refers to history of dialog with the user recognized in voice recognition to recognize that the user has had a busy life. The dialog history may include, for example, the time in which utterance was given, and the content of utterance. Cleaning robot 211 utters "You must have been tired." The user recognizes the utterance and replies "Yeah, I've been busy at work." Cleaning robot 211 recognizes the reply and then diagnoses the user. As described above, this diagnosis may be performed in the inside of cleaning robot 211 or in an external server device (for example, provider server 250) capable of receiving a voice signal from cleaning robot 211.

If detecting that the user has been fatigued more severely than before for the last two weeks, cleaning robot 211 utters "Why don't you take some days off and make a trip?" In response to the utterance, the user replies "Sure. Thanks." The user is given a suggestion from cleaning robot 211 to make a trip, and the user's fatigue or stress may be alleviated.

(Scenario 3) <Third Embodiment>

As a third embodiment, the dialog between cleaning robot 211 and the user may be used in cooperation with a medical institution. In an example, as is the case with scenario 2, cleaning robot 211 utters "You must have been tired." The user recognizes the utterance and replies "Yeah, I've been busy at work." Cleaning robot 211 recognizes the reply and then utters "Take it easy." In response to the utterance, the user replies "Sure. Thanks."

Cleaning robot 211 recognizes the reply and then transmits dialog information concerning the user's fatigue for the last two weeks, to medical institution server 230. Medical institution server 230 is a hospital or any other therapy/treatment facility in the region where the user's home 210 resides or in the neighborhood thereof. In place of the embodiment in which cleaning robot 211 transmits dialog information to medical institution server 230, provider server 250, which accumulates dialog information, may respond to a request from cleaning robot 211 to transmit the user's dialog information to medical institution server 230. A transmission request for the dialog information may be transmitted not by cleaning robot 211 but by medical institution server 230 receiving a permission from cleaning robot 211.

Medical institution server 230 diagnoses the user based on the dialog information. When determining that the user requires a doctor diagnosis, medical institution server 230 transmits such a determination result to cleaning robot 211. The determination result is created by medical institution server 230 by adding the name of the user's doctor, the date of visit, and the like to one or more predefined templates. Based on such a determination result, cleaning robot 211 utters "Psychosomatic medicine doctor Yamada says you should come for a checkup." The user responds to the utterance "I see."

Cleaning robot 211 recognizes the response and then refers to data held in advance as the doctor's consultation dates to utter "Do you want me to make an appointment at six next Wednesday?" In response to the utterance, the user replies "Please." In response to the reply, cleaning robot 211 communicates with medical institution server 230 to apply for an appointment at six p.m. next Wednesday (for example February, 12) to see the doctor. When the appointment is accepted by medical institution server 230, cleaning robot 211 utters to the user "I have made an appointment at six p.m. on February, 12, Wednesday." The user recognizes the utterance and then replies "Thank you."

In this way, in an example, cleaning robot 211 also makes an arrangement for an appointment with a medical institution in place of the user, as needed by the user. The user feels relaxed through the dialog as described above, and in addition, may appreciate cleaning robot 211 making an appointment for the user. In another aspect, an appoint on the date proposed by cleaning robot 211 may not be reserved. In this case, cleaning robot 211 may inquire medical institution server 230 about possible appointment dates and notify the user of the result of inquiry as an alternative.

(Scenario 4) <Fourth Embodiment>

As a fourth embodiment, in place of a home appliance, automobile 280 having an interactive function may interact with a driver who is a user. In one aspect, the control device of the air conditioner has an interactive function and a diagnosis function.

The control device detects that the air conditioner is switched on, and then utters "The pollen count is high today. I'll activate the air purifier," using the microphone (not shown) built in automobile 280. The pollen count being high may be acquired, for example, from weather information received by the control device of automobile 280 via the Internet 30. In response to the utterance, the driver replies "Thank you." The air conditioner recognizes the reply and then refers to the attribute of the driver held in the internal memory of the control device to utter "How's your hay fever, today?" In response to the utterance, the driver replies "Terrible, today." The air conditioner recognizes the meaning of the reply and then utters "Take care of yourself." The driver recognizes the utterance and then replies "Thank you."

In this way, the driver's stress or fatigue may be alleviated by the air conditioner speaking to the driver. In addition, the air purifier is activated in response to the content of the conversation, which may also contribute to alleviation of stress or fatigue. The driver's reply may not be recognized by the air conditioner. For example, in another embodiment, automobile 280 may connect to the Internet 30 so that provider server 250 or other external information processing device recognizes the reply. Automobile 280 and smartphone 260 owned by the driver may configure a communication session via WiFi (Wireless Fidelity), Bluetooth®, or any other communication means so that smartphone 260 recognizes the driver's conversation.

In another embodiment, output of a sensor mounted on automobile 280 may be used. For example, it may be estimated from the vehicle speed obtained by a vehicle speed sensor that the user's mental state is high. Alternatively, if the accelerator pedal depressing rate exceeds a normal rate, or if a harsh braking or an abrupt steering operation is performed, it may be estimated that the user's mental state is unusual. In such a case, automobile 280 may utter so as to ease the user's mind. Alternatively, in another aspect, automobile 280 may replay music or emit fragrance for that purpose.

(Scenario 5) <Fifth Embodiment>

As a fifth embodiment, automobile 280 may operate so as to prompt the user to act, based on the conversation with the user.

In an embodiment, the controller of automobile 280 detects that the driver's seat belt is fastened, and then utters "You seem to suffer from terrible hay fever today." The driver recognizes the utterance and then replies "Sure." The controller acquires the meaning of the reply through the internal voice recognition and analysis processing or through recognition processing by an external information processing device connected to the Internet 30, and then utters "Keep the window closed. I'll activate the air purifier" through the speaker (not shown). The driver recognizes the utterance and then replies "Thank you." Alternatively, the speaker may utter "I'll close the window and activate the air purifier," and the controller may automatically close the window and activate the air purifier.

In this way, automobile 280 starts uttering to the driver, whereby the driver may feel attention of the automobile 280 and the driver's fatigue or stress may be alleviated.

(Scenario 6) <Sixth Embodiment>

As a sixth embodiment, each home appliance provided in home 210 may communicate with a home appliance in another home 220 or another smartphone 270 through the Internet 30. In the following description, the resident (Grandma) of home 210 and the resident (Mom) of home 220 are family.

In an aspect, Grandma living in home 210 performs a switch operation or gives an utterance to cleaning robot 211. In response to such Grandma's action, cleaning robot 211 starts cleaning while running on its own.

In order to reduce the operating sound, cleaning robot 211 temporarily stops during cleaning and utters "Thank you always for using me." In response to the utterance, Grandma replies "Thank you, too." Cleaning robot 211 identifies that the utterer is Grandma, and refers to the history of dialog with Grandma in response to the recognition result of the meaning of the reply. Cleaning robot 211 detects that the word "tired" is frequently used in the latest utterances of Grandma, based on the history. Cleaning robot 211 then utters "Grandma, you've often said I'm tired." Grandma recognizes the utterance and then replies "Right. I get tired for no reason." Cleaning robot 211 acquires the recognition result of the meaning of the reply and then extracts the keyword "tired" from the reply. In an aspect, such a keyword may be stored in cleaning robot 211 or other home-appliance system itself. In another aspect, keywords may be registered with the provider or the local government that provides "monitoring care service".

In response to detection of the keyword "tired", cleaning robot 211 refers to the database held in the internal memory to calculate the frequency of use of the keyword "tired". Cleaning robot 211 detects that the count of use of the word "tired" exceeds a certain number (for example, 30 times) in a predefined period (for example, two weeks). In response to such a detection result, cleaning robot 211 communicates with the central control unit of the interactive home-appliance system at home 220. In an aspect, the central control unit may be implemented in a home server device provided in home 220 or by a control device of cleaning robot 221 or other home appliances. In another aspect, the central control unit may be provided in local government server 240.

For example, cleaning robot 221 serves as the central control unit to receive the detection result and then starts communicate with smartphone 260 of "Mom" who is a resident of home 220. Cleaning robot 221 transmits a message to smartphone 260. Smartphone 260 receives the message through the Internet 30 and then utters, in place of cleaning robot 211, "This is the vacuum cleaner at Grandma. Grandma says 'I'm tired' as often as 30 times in these two weeks" and "Grandma is now at home. Do you want me to call Grandma?" Mom recognizes the utterance and then replies "Please." Then, smartphone 260 calls cleaning robot 211 having the enabled Internet telephone, for example, using VoIP (Voice over Internet Protocol). When Grandma answers the call, Mom can talk with Grandma.

In this way, the operation of cleaning robot 211 triggers a dialog between the user (Grandma) of cleaning robot 211 and her family (Mom) who lives at a distance, whereby Grandma's loneliness, fatigue, and the like may be alleviated.

Seventh Embodiment

In another aspect, as a seventh embodiment, local government server 240 used by the local government that provides monitoring care service may function as the central control unit. In this case, cleaning robot 211 transmits to local government server 240 a message including the keyword "tired" and the identifier of the utterer (Grandma living in home 210).

The processor of local government server 240 receives the message and then accesses a resident database to add the content of the message to the record of Grandma living in home 210. The processor counts the number of times "tired" or any other keyword is received, and detects that the count of use of the word "tired" exceeds a certain number (for example, 30 times) in a predefined period (for example, two weeks). In response to such a detection result, the processor transmits a message for utterance to smartphone 260 of Mom registered in local government server 240 as an applicant for the monitoring care service. Smartphone 260 receives the message and then utters "This is the vacuum cleaner at Grandma. Grandma says 'I'm tired' as often as 30 times in these two weeks" and "Grandma is now at home. Do you want me to call Grandma?" as described above. Also in this way, Grandma's loneliness, sense of fatigue, and the like may be alleviated.

As previously mentioned, recognition of voice output by the user, extraction of the meaning, and other information processing may be performed in the inside of each individual home appliance such as cleaning robot 211. Alternatively, in another aspect, the information processing may be performed in medical institution server 230, local government server 240, provider server 250, or other external server devices.

[Configuration of Home-Appliance System]

Referring to FIG. 3, the configuration of interactive home-appliance system 20 according to the present embodiment will be described. FIG. 3 is a block diagram illustrating a detailed configuration of a server and a home appliance included in home-appliance system 20. In an aspect, home-appliance system 20 includes a server 310 and a home appliance 350.

In an embodiment, server 310 includes a communication unit 311, an appliance control signal transmitting unit 312, an appliance control unit 313, an appliance state/control command receiving unit 314, an overall control unit 315, a voice recognition unit 316, a dialog control unit 317, a voice synthesis unit 318, a person identifying unit 319, an appliance state utterance generating unit 320, an information utterance generating unit 321, a fatigue assessment utterance generating unit 322, a fatigue assessing unit 323, an assessment notification unit 324, and a personal information storing unit 325.

In an aspect, server 310 is implemented, for example, by a computer having a well-known configuration. In server 310, communication unit 311 includes, for example, an interface for communicating with home appliance 350. Appliance control signal transmitting unit 312 generates a signal for controlling home appliance 350 and transmits the signal to home appliance 350 through communication unit 311.

Appliance control unit 313 is configured to control home appliance 350 when a preset condition is established or when an instruction is received. The condition is, for example, that the keyword (for example, "tired") registered in advance is used in the contents of the user's utterances a certain number of times in a certain period. The instruction may be transmitted by another information communication terminal (for example, cleaning robots 211, 221, smartphone 260) capable of communicating with server 310.

Appliance state/control command receiving unit 314 receives a command for controlling home appliance 350 from an external service. For example, appliance state/control command receiving unit 314 receives a voice signal for allowing cleaning robot 211 to utter. In another aspect, appliance state/control command receiving unit 314 receives a signal indicating the appliance state transmitted by home appliance 350.

Overall control unit 315 controls the operation of server 310. In another aspect, overall control unit 315 controls the operation of the home appliance capable of communicating with home appliance 350 and other servers, based on a signal applied to server 310.

Voice recognition unit 316 analyzes the voice signal received from home appliance 350 and recognizes the meaning based on the analysis result. The voice signal includes, for example, a signal indicating the conversation of the user or the driver with the cleaning robot 211 or automobile 280.

Dialog control unit 317 controls an utterance and a dialog with an utterer for home appliance 350. More specifically, dialog control unit 317 selects the content of utterance to be output by home appliance 350 next time, from a database prepared in advance, based on the result of recognition by voice recognition unit 316, and transmits data (voice signal, identification number of utterance, and the like) for implementing the selected utterance to home appliance 350.

Voice synthesis unit 318 generates voice to be uttered by home appliance 350, based on a signal sent from dialog control unit 317. The generated signal is then sent to home appliance 350 through communication unit 311.

Person identifying unit 319 determines whether the user of home appliance 350 is a user registered in advance in server 310, based on a signal received from home appliance 350 or data provided from an external service. The result of the determination is sent to dialog control unit 317. Dialog control unit 317 controls a dialog with the user through home appliance 350, based on the result of the determination.

Appliance state utterance generating unit 320 generates a content to be uttered by home appliance 350, in accordance with the state of home appliance 350. The state is specified based on an instruction given to home appliance 350.

Information utterance generating unit 321 generates a content to be uttered by home appliance 350, based on data sent from an external service. For example, information utterance generating unit 321 includes an utterance of home appliance 350 for asking about the health, and an utterance for obtaining information related to the health (for example, symptoms of hay fever).

Fatigue assessment utterance generating unit 322 generates an utterance (for example, "You must have been tired") for assessing whether the user of home appliance 350 is fatigued, based on data held in advance in server 310.

Fatigue assessing unit 323 assesses whether the utterer of a reply is fatigued, based on the reply (for example, "Yeah. I've been busy at work") to the content uttered by fatigue assessment utterance generating unit 322 and the dialog history data held in server 310. Fatigue assessing unit 323 stores the result of assessment in association with the user, into personal information storing unit 325.

Personal information storing unit 325 stores information of the user of home appliance 350 or others. The information includes, for example, the result of assessment by fatigue assessing unit 323, each user's voice print, fingerprint, image information, and other data, and dialog history for each user. The dialog history includes identification information of the content uttered by home appliance 350, the user's reply to the utterance, and data of the date and time when the dialog is made.

Assessment notification unit 324 transmits the assessment result held in personal information storing unit 325 to an external service.

The configuration for implementing server 310 is implemented by one or more processors, an instruction for implementing the configuration, and a communication interface. In another aspect, server 310 may be implemented by circuit elements for implementing the configuration.

[Configuration of Home Appliance]

Referring to FIG. 3 again, home appliance 350 includes a communication unit 351, an overall control unit 352, a control command receiving unit 353, a state acquiring unit 354, a personal information acquiring unit 355, an appliance control unit 356, a voice acquisition control unit 357, an utterance control unit 358, and a state display unit 359.

Communication unit 351 is configured to be able to communicate with communication unit 311 of server 310. Overall control unit 352 controls the operation of home appliance 350. Control command receiving unit 353 accepts input of operation by the user of home appliance 350. In another aspect, control command receiving unit 353 receives a control signal sent from server 310.

State acquiring unit 354 acquires the state of operation of home appliance 350. The acquired information may be transmitted by overall control unit 352 from communication unit 351 to server 310.

Personal information acquiring unit 355 acquires personal information of the user of home appliance 350, based on operation or input to home appliance 350. The personal information may include the user's voice print, face image, fingerprint, and other biological information unique to the user, the user's name, and other character information. In an aspect, personal information acquiring unit 355 may be implemented by a microphone and a voice recognition processing program for acquiring the user's voice print. In another aspect, personal information acquiring unit 355 may be implemented by a camera and a face recognition program. In yet another aspect, personal information acquiring unit 355 may be implemented by a fingerprint sensor.

Appliance control unit 356 operates based on a signal sent from server 310. The operation of home appliance 350 is controlled in accordance with control of overall control unit 352. In another aspect, appliance control unit 356 executes a predefined operation for each operation or content, in response to the operation or the content of utterance by the user of home appliance 350.

Voice acquisition control unit 357 acquires the user's utterance to home appliance 350 and subjects the utterance to voice processing to acquire a voice signal. Voice acquisition control unit 357 transmits the acquired signal to overall control unit 352. Overall control unit 352 may transmit the content of utterance given to home appliance 350 to server 310 through communication unit 351.

Utterance control unit 358 executes utterance in response to an instruction by server 310, based on a signal received by communication unit 351. In another aspect, utterance control unit 358 implements an initial question by cleaning robot 211 or other home appliance 350, as shown in the foregoing scenario 1 to scenario 6.

State display unit 359 executes display indicating the operation of home appliance 350, based on an instruction from overall control unit 352. The display may include, for example, display with an LED (Light Emitting Diode) or display on a liquid crystal monitor. The content of the display may include display indicating that home appliance 350 is implementing a usual home appliance function, display indicating having a dialog with a user, and display indicating that home appliance 350 starts a dialog with a user and the operation mode is a mode of diagnosing the state of stress or fatigue.

[Control Structure of Home-Appliance System]

Referring to FIG. 4, a control structure of home-appliance system 20 according to the present embodiment will be described. FIG. 4 is a flowchart illustrating part of the processing in home-appliance system 20.

At step S410, home-appliance system 20 accepts registration of appliances (for example, cleaning robot 211, refrigerator 213, and other home appliance 350) on the cloud side, for example, in server 310.

At step S420, home-appliance system 20 accepts registration of external equipment on the cloud side (server 310) or in home appliance 350. Examples of the external equipment may include smartphones 260, 270, automobile 280, other home appliances, medical institution server 230, local government server 240, provider server 250, and other information processing communication devices.

At step S430, home-appliance system 20 awaits occurrence of an event. In an example, the event may include an event produced in the inside of home-appliance system 20, an event for controlling home appliance 350, and voice input that is input in home-appliance system 20. The event produced in the inside of home-appliance system 20 may include an event produced in home appliance 350 (for example, a condition that cleaning robot 211 should speak to the user is established as a result of referring to dialog history). The event for controlling home appliance 350 may include detection of a control signal sent from medical institution server 230, local government server 240, provider server 250, or the like, and the driver of automobile 280 starting driving. The voice input may include, for example, the user speaking to cleaning robot 211.

(Occurrence of Internal Event)

At step S440, home-appliance system 20 determines reaction processing in response to occurrence of an internal event. For example, when cleaning robot 211 serving as home appliance 350 detects that certain days have passed since speaking to the user, cleaning robot 211 gives an utterance for checking the user' state. For example, cleaning robot 211 asks the user a question, for example, “You must have been tired” (see scenario 3). Home-appliance system 20 refers to the past dialog history based on the user's reply to the question, and decides on the next reaction.

At step S442, home-appliance system 20 selects a reaction utterance. This selection is made by, for example, selecting one from among dialog utterances prepared in advance. For example, as shown in scenario 2, home-appliance system 20 selects a message “Psychosomatic medicine doctor Yamada says you should come for a checkup”.

At step S444, home-appliance system 20 executes an utterance. For example, cleaning robot 211 outputs the content of the message via voice.

At step S446, home-appliance system 20 executes defined processing in response to the utterance. For example, home-appliance system 20 communicates with medical institution server 230 to acquire an appointment for the user to see the doctor.

(Appliance Control)

At step S450, home-appliance system 20 determines reaction processing in response to a signal for appliance control. For example, as shown in scenario 4, home-appliance system 20 detects that the user switches on the air conditioner of automobile 280. In response to the signal, home-appliance system 20 starts the operation of the air conditioner.

At step S452, home-appliance system 20 selects a reaction utterance corresponding to the appliance control from among predefined reaction utterances. For example, in the case of scenario 4, the utterance “The pollen count is high today. I'll activate the air purifier” is selected as an utterance that may be given during operation of the air conditioner.

At step S454, home-appliance system 20 executes an utterance based on the selected utterance. Furthermore, home-appliance system 20 detects the user's reply (“Thank you”) returned for the utterance.

At step S456, home-appliance system 20 executes defined processing corresponding to the utterance (for example, switch on the air purifier). In addition, home-appliance system 20 utters, as a next utterance, “How's your hay fever today?”

(Voice Input)

At step S460, home-appliance system 20 recognizes the voice input to home appliance 350 (in the case of scenario 1, “I'm back”).

At step S462, home-appliance system 20 understands the content meaning of the utterance. Home-appliance system 20 determines whether the utterance content is an utterance registered in advance in the database.

At step S464, home-appliance system 20 determines reaction processing, based on the result of the determination. For example, when an utterance registered in the database is given, it is further determined whether to make a diagnosis, based on the history of dialog with the user.

At step S466, home-appliance system 20 selects a reaction utterance. For example, home-appliance system 20 selects an utterance "You must have been tired."

At step S468, home-appliance system 20 executes an utterance based on the selected utterance. For example, cleaning robot 211 utters "You must have been tired."

At step S470, home-appliance system 20 executes defined processing corresponding to the utterance. For example, when the user replies "Yeah, I've been busy at work," home-appliance system 20 executes voice recognition processing and meaning analyzing processing to detect that the keyword "busy" is extracted. If the count of use of the keyword within a predetermined certain period exceeds a predetermined number of times, home-appliance system 20 utters, "Take it easy."

Referring to FIG. 5, the control structure of home-appliance system 20 will be further described. FIG. 5 is a flowchart illustrating part of the processing executed by home appliance 350 and server 310 included in home-appliance system 20.

(Appliance Side)

At step S510, overall control unit 352 of home appliance 350 accepts registration of appliances. The appliances to be registered include home appliance 350 itself. More specifically, in an example, overall control unit 352 accepts, for example, registration of refrigerator 213, light 214, television 215, air conditioner 216, and other home appliances installed in home 210, and automobile 280 that may be used by the residents of home 210. Overall control unit 352 stores the identification number of each home appliance into the internal memory of home appliance 350.

At step S512, overall control unit 352 accepts registration of external equipment. External equipment includes, for example, equipment capable of communicating with home appliance 350, such as medical institution server 230, local government server 240, provider server 250, and server 310.

At step S514, overall control unit 352 awaits occurrence of an event in home appliance 350. The occurrence of an event may include any of an internal event, appliance control, and voice input.

At step S516, overall control unit 352 detects occurrence of an internal event. Home appliance 350 transmits a signal to server 310 to indicate that an internal event has occurred. Server 310 receives such a signal to detect that an internal event has occurred in home appliance 350. Home appliance 350 thereafter receives utterance information corresponding to the internal event from server 310.

At step S518, overall control unit 352 detects occurrence of an event based on appliance control. Home appliance 350 transmits a signal to server 310 to indicate that the event based on appliance control has occurred. Server 310 receives such a signal to detect that an event based on control of home appliance 350 has occurred in home appliance 350. Home appliance 350 thereafter receives utterance information corresponding to the event based on control of home appliance 350 from server 310.

At step S520, overall control unit 352 detects occurrence of an event based on voice input. Home appliance 350 transmits a signal to server 310 to indicate that the event based on voice input has occurred. Server 310 receives such a signal to detect that an event based on voice input to home appliance 350 has occurred. Home appliance 350 thereafter receives utterance information corresponding to the event based on voice input from server 310.

At step S522, home appliance 350 utters through utterance control unit 358, based on the utterance information received from server 310. The content of the utterance is, as shown in the above-noted scenarios, for example, "You must have been tired," "The pollen count is high today. I'll activate the air purifier," or the like.

At step S524, home appliance 350 executes the operation of home appliance 350 in accordance with processing information, through appliance control unit 356, based on the content of processing information received from server 310.

(Cloud Side)

At step S540, overall control unit 315 of server 310 accepts registration of home appliance 350. Server 310 receives input of the identification information, the name, and the like of home appliance 350 for storage into the internal memory.

At step S542, overall control unit 315 accepts registration of external equipment. The external equipment is a device capable of communicating with server 310, such as medical institution server 230, local government server 240, and other information processing communication devices.

At step S544, overall control unit 315 receives a signal indicating occurrence of an event sent by home appliance 350, through communication unit 311 (steps S516, S518, S520).

At step S546, overall control unit 315 executes a reaction corresponding to the signal indicating the event that has occurred in home appliance 350.

(Internal Event or Appliance Control)

For example, at step S550, overall control unit 315 detects that the signal of an internal event in home appliance 350 or appliance control has been received. The control then proceeds to step S570.

(Voice Input to Home Appliance 350)

On the other hand, at step S560, overall control unit 315 receives voice corresponding to the utterance given to home appliance 350, through communication unit 311 and voice recognition unit 316.

At step S562, overall control unit 315 recognizes the received voice through voice recognition unit 316.

At step S564, overall control unit 315 understands the meaning of the utterance, based on the analysis result of the meaning of the voice. The control proceeds to step S570.

At step S570, overall control unit 315 determines reaction processing, based on the analysis result of the signal received from home appliance 350. For example, overall control unit 315 decides on the kind of utterance to be executed by home appliance 350. The kinds of utterance may include an utterance asking about the user's health, an utterance asking about the weather, and an utterance suggesting a trip.

At step S572, overall control unit 315 selects an utterance corresponding to the event, through dialog control unit 317.

At step S574, overall control unit 315 transmits utterance information corresponding to the selected utterance to home appliance 350 through communication unit 311. Communication unit 351 of home appliance 350 receives the utterance information (step S522).

At step S576, overall control unit 315 transmits processing information for allowing home appliance 350 to execute an operation, to home appliance 350 through communication unit 311. Communication unit 351 of home appliance 350 receives the processing information (step S524).

[Control Structure]

Referring to FIG. 6, the control structure of home-appliance system 20 will be further described. FIG. 6 is a flowchart illustrating part of the processing executed by server 310 to understand the meaning of an utterance to home appliance 350 in home-appliance system 20. In an aspect, home appliance 350 and server 310 are permanently connected through the Internet 30.

At step S610, overall control unit 315 selects an operation mode of server 310. Operation modes may include a general utterance mode and an utterance mode for diagnosing fatigue stress.

At step S620, overall control unit 315 selects the fatigue stress-diagnosing utterance mode. For example, when it is detected that the general utterance mode continues for a predefined certain time, overall control unit 315 selects the fatigue stress-diagnosing utterance mode.

At step S622, overall control unit 315 transmits a fatigue stress-diagnosing utterance to home appliance 350 through communication unit 311 (for example, see scenario 3). Fatigue assessment utterance generating unit 322 generates an utterance for diagnosing fatigue stress. This is generated by referring to, for example, dialog history held in personal information storing unit 325.

At step S624, overall control unit 315 selects dialog processing. For example, overall control unit 315 may select a dialog for prompting the user to receive a doctor's diagnosis, from the work life of the user of home appliance 350 (see scenario 3).

At step S626, overall control unit 315 transmits information corresponding to the selected processing to home appliance 350.

At step S628, overall control unit 315 receives a voice signal including the user's utterance to home appliance 350, from home appliance 350 through communication unit 311.

At step S630, overall control unit 315 recognizes the signal sent from home appliance 350, through voice recognition unit 316.

At step S632, overall control unit 315 understands the meaning based on the result of recognition by voice recognition unit 316. For example, overall control unit 315 detects that the user's utterance includes the keyword "tired".

At step S634, fatigue assessing unit 323 assesses the degree of fatigue stress. This assessment is made based on data stored in personal information storing unit 325 and data sent from overall control unit 315. In an aspect, fatigue assessing unit 323 may determine that the degree of user's stress is such a degree that requires an examination by a doctor when it is detected that the number of times the keyword "tired" is used, as detected from the latest user's utterances in a predefined certain period of time, exceeds a predefined number of times.

At step S636, fatigue assessing unit 323 stores fatigue stress dialog information into personal information storing unit 325. For example, the information of date and time when the use of keyword "tired" is detected is held in personal information storing unit 325.

At step S638, fatigue assessing unit 323 determines the degree of fatigue stress of the person who utters to home appliance 350, in a comprehensive manner, based on the utterance sent from home appliance 350 and data stored in personal information storing unit 325. For example, when the frequency of use of the keyword "tired" and the time interval between detection of the keyword "tired" is becoming short, fatigue assessing unit 323 determines that the degree of fatigue stress is becoming high. If the interval is becoming long, fatigue assessing unit 323 determines that the degree of fatigue stress is becoming low.

At step S640, overall control unit 315 selects an operation mode of server 310 again. For example, overall control unit 315 may continuously select the fatigue stress-diagnosing utterance mode as an operation mode of server 310.

At step S642, overall control unit 315 selects a reaction utterance to the reply made by the user of home appliance 350.

At step S644, overall control unit 315 transmits utterance information to home appliance 350 through communication unit 311, in accordance with the selection result of a reaction utterance.

At step S646, overall control unit 315 transmits, to home appliance 350, processing information for allowing home appliance 350 to operate based on the selected reaction utterance.

On the other hand, at step S660, overall control unit 315 selects the general utterance mode. When the user utters to home appliance 350, home appliance 350 recognizes the utterance and transmits a signal corresponding to the utterance to server 310. Server 310 analyzes the meaning of the utterance and transmits a signal corresponding to the result of analysis to home appliance 350. Home appliance 350 receives the signal and then outputs voice in accordance with the signal. The user recognizes the voice, whereby a normal dialog between home appliance 350 and the user may be implemented.

[Hardware Configuration]

Figure 7:
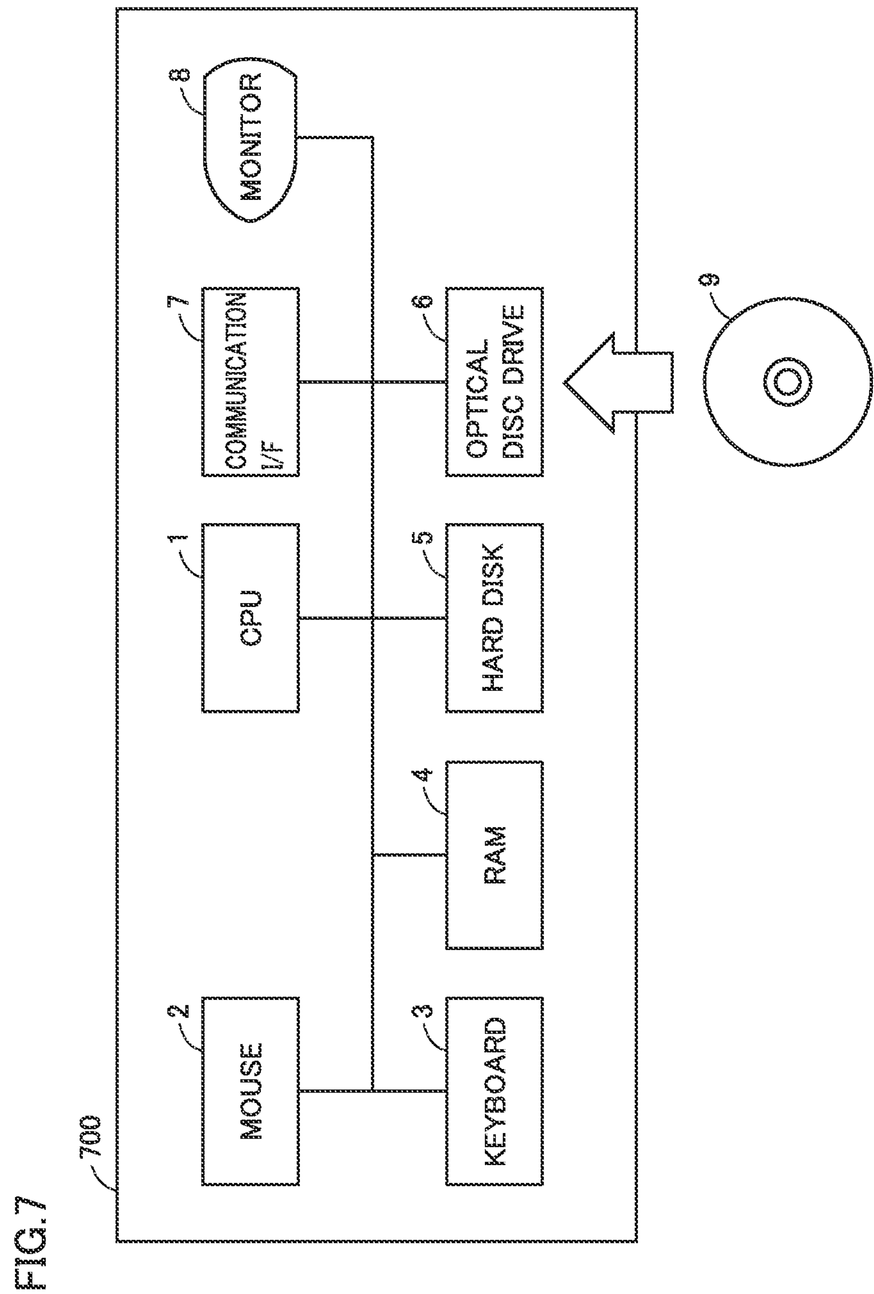
FIG. 7 is a block diagram illustrating the hardware of computer 700 for implementing an information processing communication device.

Referring to FIG. 7, a configuration of an information processing communication device according to the present embodiment will be described. FIG. 7 is a block diagram illustrating the hardware of a computer 700 for implementing an information processing communication device. In the present embodiment, the information processing communication device is equivalent to, for example, medical institution server 230, local government server 240, provider server 250, and server 310.

Computer 700 includes, as main components, a CPU (Central Processing Unit) 1 for executing a program, a mouse 2 and a keyboard 3 for accepting input of a command by the user of computer 700, a RAM 4 for volatilely storing data generated by CPU 1 executing a program or data input through mouse 2 or keyboard 3, a hard disk 5 for storing data in a nonvolatile manner, an optical disc drive 6, a monitor 8, and a communication IF (interface) 7. The components are mutually connected via a bus. CD-ROM 9 or other optical discs are attached to optical disc drive 6. Communication interface 7 includes, but not limited to, a USB (Universal Serial Bus) interface, a wired LAN (Local Area Network), a wireless LAN, and a Bluetooth® interface.

The processing in computer 700 is implemented by hardware and software executed by CPU 1. Such software may be stored in hard disk 5 in advance. The software may be distributed as a program product stored in CD-ROM 9 or other computer-readable nonvolatile data recording media. Alternatively, the software may be provided as a downloadable program product by an information provider connected to the Internet or other networks. Such software is read by optical disc drive 6 or other data readers from the data recording medium or downloaded through communication interface 7 and then temporarily stored into hard disk 5. The software is read from hard disk 5 by CPU 1 and stored into RAM 4 in an executable program format. CPU 1 executes the program.

The components of computer 700 shown in FIG. 7 are general. Therefore, it can be said that the essential part that implements the technical concept according to the present embodiment is the program stored in computer 700. The operation of hardware of computer 700 is well known and a detailed description thereof will not be repeated.

Examples of the data recording medium are not limited to CD-ROMs, FDs (Flexible Disk), and hard disks, and may include magnetic tapes, cassette tapes, optical discs (MOs (Magnetic Optical Disc)/MDs (Mini Disc)/DVDs (Digital Versatile Disc)), IC (Integrated Circuit) cards (including memory cards), optical cards, and nonvolatile data recording media that fixedly carry programs, such as semiconductor memories such as mask ROMs, EPROMs (Electronically Programmable Read-Only Memory), EEPROMs (Electronically Erasable Programmable Read-Only Memory), and flash ROMs.

As used herein, the program includes not only a program directly executable by a CPU but also a program in a source program format, a compressed program, and an encrypted program.

[Configuration of Cleaning Robot]

Referring to FIG. 8, a configuration of cleaning robots 211, 221 according to the present embodiment will be described. FIG. 8 is a block diagram illustrating a hardware configuration of cleaning robots 211, 221. Although a configuration of cleaning robot 211 is described below, cleaning robot 221 has a similar configuration.

Cleaning robot 211 includes a communication unit 801, a control unit 802, a microphone 803, a speaker 804, a cleaning unit 805, a drive unit 806, a display unit 808, and a storage unit 809. Control unit 802 includes a voice recognition unit 811, a response processing executing unit 812, an operation mode switching unit 813, and a voice input accepting unit 814. Storage unit 809 includes an utterance content database 820.

Control unit 802 controls the operation of cleaning robot 211. In an aspect, control unit 802 is implemented by a processor or other operation processing devices.

Display unit 808 displays a state of cleaning robot 211. Display unit 808 includes a liquid crystal monitor, an organic EL (Electro Luminescence) monitor, and other display devices.

Storage unit 809 holds a program for causing cleaning robot 211 to execute a predefined operation, history of the user's utterance to cleaning robot 211, and the like. In an aspect, storage unit 809 may be implemented by a flash memory, a hard disk, or other nonvolatile data recording media, or a RAM or other volatile data recording media.

In an example, communication unit 801 can wirelessly connect to the Internet 30 to communicate with network home appliances and other communicable home appliances. Microphone 803 accepts an utterance to cleaning robot 211. Speaker 804 outputs voice based on control of control unit 802.

Cleaning unit 805 includes a brush, a compressor, and other mechanisms for implementing vacuum cleaner capability. Drive unit 806 includes wheels and other mechanisms for allowing cleaning robot 211 to run.

In control unit 802, voice recognition unit 811 recognizes an utterance to cleaning robot 211, based on a signal output from microphone 803. Response processing executing unit 812 decides on an operation of cleaning robot 211, based on the result of voice recognition unit 811. In another aspect, response processing executing unit 812 may decide on response processing based on a signal received through communication unit 801.

Operation mode switching unit 813 switches the operation modes of cleaning robots 211, 221, based on a signal output from microphone 803 or a signal received through communication unit 801. In an example, the operation modes may include, for example, a normal cleaning mode and a dialog mode.

Voice input accepting unit 814 accepts input of utterance voice performed on microphone 803. In another aspect, voice input accepting unit 814 accepts input of a voice signal received through communication unit 801.

In storage unit 809, utterance content database 820 holds contents in advance for allowing cleaning robots 211, 221 to utter. In another aspect, utterance content database 820 may hold utterance contents unique to the users of cleaning robots 211, 221.

Referring to FIG. 8 again, cleaning robot 211 may be connected to the Internet 30. Provider server 250 is connected to the Internet 30. Cleaning robot 211 thus can communicate with provider server 250 on the cloud side. Provider server 250 is implemented by, for example, a computer having a well-known configuration as shown in FIG. 7. Provider server 250 includes a communication unit 251, a control unit 252, and a storage unit 256.

Communication unit 251 includes a communication interface 7. Communication unit 251 communicates with cleaning robot 211. Communication is not limited to particular manners and protocols.

Control unit 252 includes a voice input receiving unit 253, a voice recognition unit 254, and a response processing execution instructing unit 255. Control unit 252 includes a CPU 1. CPU 1 executes an instruction to enable CPU 1 to function as voice input receiving unit 253, as voice recognition unit 254, or as response processing execution instructing unit 255. In another aspect, any of voice input receiving unit 253, voice recognition unit 254, and response processing execution instructing unit 255 may be configured as a dedicated processing circuit or other circuits.

Voice input receiving unit 253 receives a voice signal input accepted in cleaning robot 211 through communication unit 251. Voice recognition unit 254 recognizes the content of the voice signal sent from cleaning robot 211. Response processing execution instructing unit 255 generates processing for responding to cleaning robot 211, based on the recognition result of the signal sent from cleaning robot 211, and transmits the processing signal to cleaning robot 211 through communication unit 251. Cleaning robot 211 receives the processing signal and then utters voice in accordance with the processing signal.

Storage unit 256 is implemented by, for example, hard disk 5. Storage unit 256 includes an utterance content database 258 and a state storing unit 259. Utterance content database 258 holds contents in advance for uttering through speaker 804 of cleaning robots 211, 221. State storing unit 259 holds the states of cleaning robots 211, 221 and the states of the users of cleaning robots 211, 221.

[Control Structure of Server]

(Server-Side Basic Flow)

Referring to FIG. 9 to FIG. 10, the control structure of server 310 according to an aspect will be described. FIG. 9 is a flowchart illustrating an example of voice recognition processing executed by server 310 to understand the meaning of an utterance and to select a message for dialog. Server 310 includes, for example, such a configuration as computer 700. FIG. 10 is a diagram illustrating an embodiment of the structure of the database in server 310.

At step S910, CPU 1 of computer 700 receives voice sent from home appliance 350 through communication interface 7.

At step S920, CPU 1 serves as voice recognition unit 316 to recognize the voice received from home appliance 350 and acquire a character string (also referred to as "input phrase") indicating the recognized content. The voice recognition processing is not limited to a particular manner.

Furthermore, CPU 1 specifies an utterer (user) for home appliance 350, based on user information registered in server 310.

At step S930, CPU 1 analyzes the character string (input phrase) and interprets the intention of the user of home appliance 350.

At step S940, CPU 1 acquires, from RAM 4 or hard disk 5, the current operation mode for each user of home appliance 350 (for example, all the residents of home 210 who have been registered as users to receive provision of service by server 310).

At step S950, CPU 1 selects an operation mode. The operation modes to be selected may include a normal dialog mode and a diagnosis mode. In an aspect, CPU 1 selects an operation mode based on whether a condition for proceeding to the diagnosis mode is established. For example, whether it is necessary to proceed to the diagnosis mode is determined by referring to the history of dialog with the user specified at step S920. For example, in order to determine the necessity to proceed to the diagnosis mode, CPU 1 determines whether the keyword that is detected in the past dialogs for the time since the last diagnosis mode is executed and that may be related to diagnosis is detected in the present utterance. When selecting the normal dialog mode, CPU 1 switches the control to step S960. When selecting the diagnosis mode, CPU 1 switches the control to step S1100.

At step S960, CPU 1 decides on a response content. In the normal dialog mode, server 310 generates a response based on the input phrase and gives voice utterance. First, CPU 1 decides on a content of the response. The response is not limited to voice and, in another aspect, may include motion of home appliance 350 and turning on and off of the light (not shown) of home appliance 350.

More specifically, referring to FIG. 10, CPU 1 refers to a response content table 1000 and an input phrase table 1010 stored in hard disk 5. Response content table 1000 includes an input phrase ID for specifying an input phrase and a specific input phrase 1002. Input phrase table 1010 includes a response ID 1011 for identifying a response by home appliance 350, an input phrase ID 1012 indicating an input phrase associated with the response, an utterance message 1013 indicating the content of a specific utterance by home appliance 350, and an operation pattern 1014 for identifying the operation of home appliance 350. Operation patterns A to C may include, for example, a normal operation, a rotating operation, and other operations.

CPU 1 selects an utterance message 1013 corresponding to the input phrase. For example, when a plurality of utterance messages exist as choices for the same input phrase, CPU 1 selects one utterance message from among the plurality of utterance messages, for example, at random. For example, when the user extends a greeting "Good morning" to home appliance 350, CPU 1 selects one utterance message at random from among three responses, namely, response IDs=1 to 3, as a response to the greeting.

Referring to FIG. 9 again, at step S962, CPU 1 assesses whether to start the diagnosis mode. The conditions for starting the diagnosis mode include, for example, the following:

- the content of the first conversion on the day between the user and home appliance 350;
- negative evaluation of the input phrase (see FIG. 12).

This enables server 310 to naturally start diagnosis of the state of the user's stress or fatigue while the user has an ordinal conversation with home appliance 350 every day. If it is assessed to start the diagnosis mode, CPU 1 may start diagnosis mode processing (step S1100) described later.

At step S980, CPU 1 synthesizes voice using a character string of the decided utterance message and generates voice data to be uttered by home appliance 350.

At step S990, CPU 1 transmits response information including voice data and operation pattern 1014 corresponding to the selected utterance message, to home appliance 350. Home appliance 350 receives the response information, then gives an utterance based on the voice data and performs an operation in accordance with operation pattern 1014. Thus, a dialog between the user and home appliance 350 is implemented, and the user's fatigue or stress may be alleviated in accordance with the content of the utterance of home appliance 350.

If CPU 1 determines to select the diagnosis mode, CPU 1 executes diagnosis mode processing described later, at step S1100.

The process then returns to step S910.

[Control Structure and Data Structure of Server]

(Diagnosis Mode Start Processing Flow)

Figure 11:
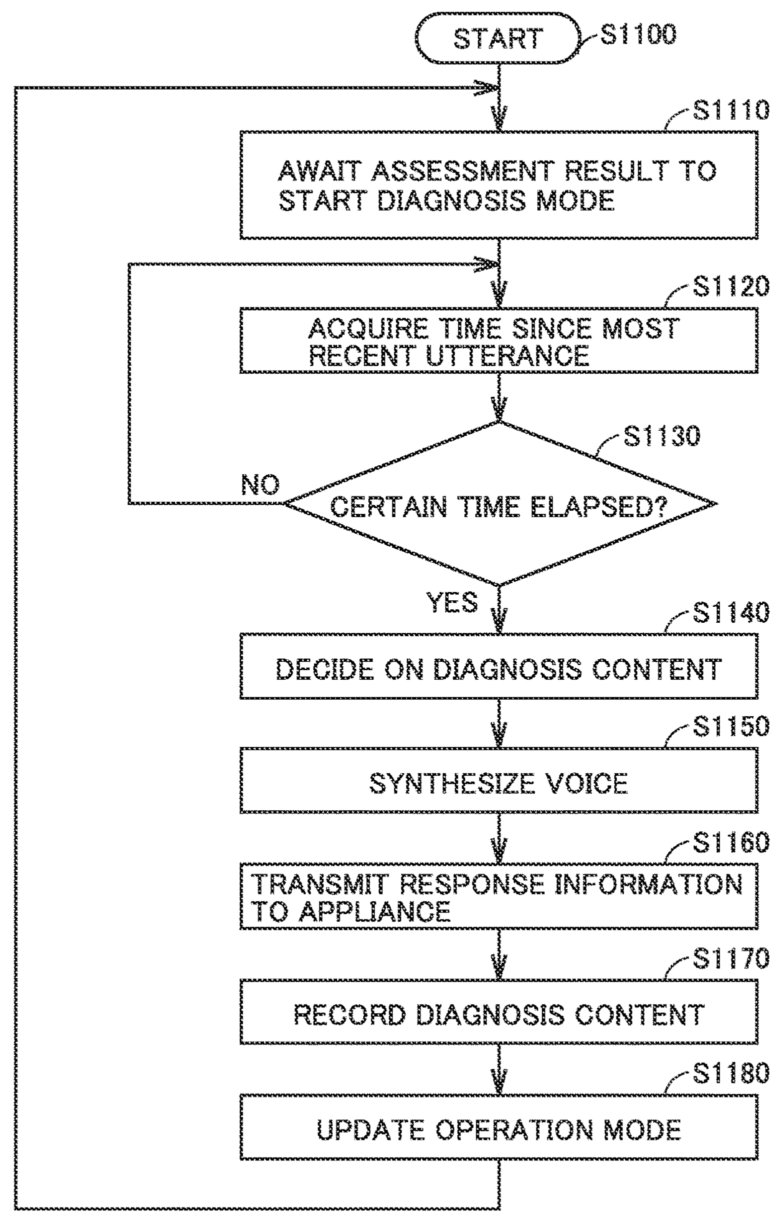
FIG. 11 is a flowchart illustrating an example of the processing executed by server 310 during a diagnosis mode.

Referring to FIG. 11 and FIG. 12, the control structure of server 310 in an aspect will be further described. FIG. 11 is a flowchart illustrating an example of the processing executed by server 310 during the diagnosis mode. In an embodiment, when server 310 starts the diagnosis mode, home appliance 350 starts a question to the user, unlike a normal dialog. Therefore, this processing is executed independently of the main processing (FIG. 9). It may be executed asynchronously with the main processing when CPU 1 determines to start the diagnosis mode in the main processing.

FIG. 12 is a diagram conceptually illustrating an embodiment of storage of data for diagnosis in hard disk 5. Hard disk 5 stores a diagnosis message table 1210 and a diagnosis history table 1220. Diagnosis message table 1210 includes a diagnosis ID 1211 for identifying the content of diagnosis, a diagnosis message 1212 having a character string representing a questions to users, and the terms of validity 1213 of the diagnosis message. For example, once the diagnosis message "Do you have an appetite?" with diagnosis ID=4 is selected, this diagnosis message cannot be selected until seven days have passed. Diagnosis history table 1220 includes a user ID 1221 for identifying the user of home appliance 350, an input date and time 1222 at which an utterance from the user is received, a diagnosis ID 1223 for identifying the diagnosis message used, an utterance message 1224 indicating the content of the diagnosis message, an input phrase 1225 indicating the character string of the utterance from the user, and an evaluation 1226 of the utterance.

Referring to FIG. 11 again, at step S1110, CPU 1 awaits the determination result indicating to start the diagnosis mode (the procedure from step S950 to step S1100 in FIG. 9).

At step S1120, CPU 1 acquires the time elapsed since the most recent utterance, using time information from the internal clock (not shown) and data of input date and time 1222.

At step S1130, if the elapsed time is equal to or longer than a certain time (for example, one minute), CPU 1 determines that an utterance from the user of home appliance 350 is no longer produced (YES at step S1130), and the CPU starts a question to the user.

At step S1130, CPU 1 determines whether a predefined certain time has elapsed. For example, the time elapsed since the most recent utterance is equal to or longer than a preset certain time (for example, one minute), CPU 1 determines that an utterance from the user of home appliance 350 is no longer produced. If it is determined that a certain time has elapsed since the time since the most recent utterance is acquired (YES at step S1130), CPU 1 switches the control to step S1140. If not (NO at step S1130), CPU 1 returns the control to step S1120. For example, when a normal dialog between home appliance 350 and the user continues, the elapsed time should fall within the certain time. It follows that CPU 1 waits for the next processing until the dialog ends.

At step S1140, CPU 1 decides on a diagnosis content. For example, CPU 1 selects a diagnosis message 1212 at random from diagnosis message table 1210 (FIG. 12). Since it is meaningless to repeat the same question using the same diagnosis message, CPU 1 may refer also to diagnosis history table 1220 to select a diagnosis message 1212 from the choices excluding the diagnosis message used in the latest question (that is, utterance message 1224).

At step S1150, CPU 1 synthesizes voice using the character string of the selected diagnosis message and generates voice data to be uttered by home appliance 350, in the same manner as in the main processing.

At step S1160, CPU 1 transmits response information including voice data to home appliance 350.

At step S1170, CPU 1 records the diagnosis content including the selected diagnosis message and the user ID in diagnosis history table 1220 to update diagnosis history table 1220. Input phrase 1225 and evaluation 1226 are preferably blank (NULL) at this point of time, because CPU 1 will store data after receiving a response from the user.

At step S1180, CPU 1 updates the operation mode. More specifically, CPU 1 sets the operation mode of server 310 for the user to the "diagnosis mode". Therefore, when server 310 subsequently receives voice of the user of home appliance 350, CPU 1 may execute the processing in the diagnosis mode.

The control then returns to step S1110.

Server 310 may be configured to integrate the total in a certain period using the history shown in FIG. 12 or the history for a particular user. Such a configuration enables server 310 to transmit a report to the user of home appliance 350, a medical institution, a local government, or the like, as necessary.

(Diagnosis Mode Processing Flow)

Referring to FIG. 13 to FIG. 15, the control structure of home-appliance system 20 will be further described. FIG. 13 is a flowchart illustrating an example of the diagnosis mode processing executed by CPU 1. In the diagnosis mode, server 310 asks some questions to the user through home appliance 350 and diagnoses the user's fatigue or stress or other mental states based on the user's response to the questions.

FIG. 14 and FIG. 15 are diagrams conceptually illustrating an embodiment of storage of data in hard disk 5. In an example, as shown in FIG. 14, hard disk 5 holds a reply evaluation table 1400. Reply evaluation table 1400 includes a reply ID 1401 for identifying a reply from a user, a diagnosis ID 1402 for identifying diagnosis message 1212 used for a question, an input phrase 1403 indicating the character string obtained from the reply, and an evaluation 1404 indicating the result of diagnosis. Diagnosis ID 1402 corresponds to diagnosis ID 1211.

As shown in FIG. 15, hard disk 5 includes a normal message table 1510 and a healing message table 1520. Normal message table 1510 includes a message ID 1501 and a message 1502. Healing message table 1520 includes a message ID 1521 and a message 1522.

In healing message table 1520, message 1522 may be stored, which gives a sense of healing more than message 1502 included in normal message table 1510. Message 1522 that gives a sense of healing is, for example, a phrase to care about the user, a phrase to suggest an action for improving the health or alleviating stress, a phrase that makes the user laugh, and a phrase that touches the user's heart. Examples of the phrase to care about the user may include "You've been doing well," "Don't work too hard," "I'm worrying about you," and other phrases. Examples of the phrase to suggest an action for improving the health or alleviating stress may include "Why don't you go to bed early?" "Why don' you take day off tomorrow?" "You have a baseball game in town tomorrow," and other phrases. Examples of the phrase that makes the user laugh may include puns such as "futon ga futtonda" and jokes.

In another aspect, voice content 1530 for alleviating stress may be stored in server 310, in place of a message that gives a sense of healing. Examples of voice content 1530 may include data for outputting voice of animals such as dogs, cats, and birds, poetry reading, and music.

In yet another aspect, the degree of healing may be varied by changing the quality of voice between voice output based on message 1502 included in normal message table 1510 and voice output based on message 1522 included in healing message table 1520. In an embodiment of changing the quality of voice, for example, a normal message is output in a male voice, and a healing message is output in a female voice. In a case where both a normal message and a healing message are output in a female voice, a sense of healing may be enhanced by changing the tone of voice in those messages.

In another aspect, the degree of healing may be varied by changing the pitch (high/low) of output voice. In an embodiment of changing the pitch of voice, for example, the pitch of voice may be set higher than normal to cheer up as healing, or conversely, the pitch of voice may be set lower than normal to express warmth in voice as healing.

In another aspect, the degree of healing may be varied by changing the utterance speed of output voice. For example, to increase the degree of healing, the utterance speed may be set lower than normal speed to express warmth to the user. Conversely, the utterance speed may be set faster than normal to encourage the user.

In another aspect, the degree of healing may be varied by changing the volume of output voice. For example, to increase the degree of healing, voice is set quieter than usual to express warmth to the user. Conversely, voice may be set louder than normal to encourage the user.

In another aspect, the degree of healing may be varied by changing the intonation of output voice. For example, to increase the degree of healing, the intonation of the phrase "Hello" may be changed for output, for example, with a Kansai accent, thereby making the phrase friendly or humorous for the user. In yet another aspect, the aforementioned embodiments for varying the degree of healing may be selected and combined as appropriate.

In another example, a healing message table corresponding to each individual user may be configured. Such healing message tables may include, for example, a table for outputting female voice to male users and a table for outputting child voice to elderly such as grandfathers and grandmothers. In yet another aspect, when server 310 is configured to obtain latest information from another information communication device, for a user who is interested in soccer, server 310 may obtain the result of the yesterday soccer game, player performance information, and other information from the other information communication device and synthesize voice data for uttering, for example, "XX made an awesome shot yesterday." Voice synthesis can be implemented by a well-known technique and therefore a detailed description thereof will not be repeated. A healing message table may be configured corresponding to a user targeted by home appliance 350.

Referring to FIG. 13 again, at step S1310, CPU 1 refers to diagnosis history table 1220 to acquire the content of the utterance (diagnosis ID 1223) output from home appliance 350 most recently.

At step S1320, CPU 1 refers to reply evaluation table 1400 to evaluate input phrase 1403 obtained from the utterance. As an example, CPU 1 searches reply evaluation table 1400 for input phrase 1403 that matches input phrase 1225 from the user, among diagnosis IDs that match diagnosis ID 1223 of diagnosis message 1224 uttered most recently by home appliance 350. For example, edit distance is used as the degree of matching. If input phrase 1403 that matches input phrase 1225 is found, CPU 1 sets the value of evaluation 1404 associated with the input phrase 1403 as the evaluation for input phrase 1403. On the other hand, if no matching input phrase 1403 is found, CPU 1 sets the evaluation of the reply to "0".

For example, when the most recent question (utterance message 1224) is "How are you doing?" (the value "1" of diagnosis ID 1211) and the user's response to the question is "Fine," reply ID 1401=1 is matched and the evaluation for this input phrase is "+1". On the other hand, even when the user's reply is a positive reply "Yes," the evaluation may vary depending on the content of the question (for example, see the cases of reply ID 1401=7, 11). Therefore, when the user's reply "Yes" is a reply (reply ID 1401=7) to the question from home appliance 350 "Did you sleep well last night?" (diagnosis message 1212 corresponding to diagnosis ID 1211=2), the value of evaluation 1404 is "+1". On the other hand, when the reply "Yes" is a reply (reply ID=11) to the question from home appliance 350 "Do you sleep badly lately?" (diagnosis message 1212 corresponding to diagnosis ID 1211=3), the value of evaluation 1404 is "−1".

At step S1330, CPU 1 records the evaluated input phrase and the result of the evaluation as input phrase 1225 and evaluation 1226 in diagnosis history table 1220.

At step S1340, CPU 1 determines whether to continue the diagnosis mode. This determination is made, for example, based on a signal applied to server 310 and the result of the reply to home appliance 350. As a specific example, CPU 1 counts the questions during the current diagnosis mode and terminates the diagnosis mode at a point of time when a preset number of questions are made. If this number is too large, the questions are so frequent to burden the user. Therefore, for example, the number is preferably, for example, three, but the number is not limited to three and may be one. If it is determined to continue the diagnosis mode (YES at step S1340), CPU 1 switches the control to step S1350. If not (NO at step S1340), CPU 1 switches the control to step S1370.

(To Continue Diagnosis Mode)

At step S1350, CPU 1 decides on a diagnosis content for home appliance 350 to ask a next question to the user.

At step S1360, CPU 1 records the diagnosis content in diagnosis history table 1220.

(To Terminate Diagnosis Mode)

At step S1370, CPU 1 evaluates the mental state of the user of home appliance 350 based on the diagnosis result. More specifically, for example, when the value of evaluation 1226 recorded in diagnosis history table 1220 is negative in the current diagnosis mode, CPU 1 determines that the user's mental state is bad, that is, the user is having some stress or fatigue. When home appliance 350 makes a question multiple times, CPU 1 determines the user's mental state using the sum of values of evaluation 1226 for the replies to the questions.

At step S1380, CPU 1 decides on a content of response by home appliance 350 in accordance with the determination result. For example, CPU 1 refers to normal message table 1510 and healing message table 1520 to decide on a response content. If it is determined that the user's mental state is bad, CPU 1 selects a message 1522 for a response from healing message table 1520 at random. When such message 1522 is uttered by home appliance 350, the effect of improving the user's mental state can be expected. On the other hand, if it is determined that the user's mental state is not bad, CPU 1 selects a message 1502 for a response from normal message table 1510 at random.

At step S1390, CPU 1 changes the operation mode of server 310 from the diagnosis mode to the normal mode.

(History-Based Diagnosis)

The user's mental state may be diagnosed based on not only the evaluation in the current diagnosis mode but also, for example, the user's past history to enable a more effective diagnosis.

For example, the following diagnosis methods can be contemplated.

- Diagnosis using all the diagnosis results on the day (the sum of evaluation values for a day)
- Diagnosis using all the diagnosis results in a predetermined period (the sum of evaluation values for the last three days)
- Diagnosis in which an evaluation value is calculated every other day, and if the evaluation value is negative for a predetermined number of days (for example, three days) consecutively, it is determined that the user's mental state is bad.
- An evaluation value is calculated every other day, and the average of evaluation values every week is calculated. If the evaluation value in the last one week is negative, and the difference between the evaluation value in the last one week and the evaluation value in the preceding one week is equal to or greater than a predefined threshold, it is determined that the mental state tends to go bad, and it is determined that the mental state is bad.

In an embodiment illustrated above, for example, as shown in FIG. 10, FIG. 12, and FIG. 15, voice data corresponding to each message is stored as data for utterance in a storage device such as hard disk 5. However, an embodiment of storage of data for voice output is not limited to the example described above. For example, character strings and data for voice synthesis may be held in a storage device, and voice synthesis may be performed using the character string corresponding to the content of utterance, whereby a healing message is uttered as voice. Voice synthesis is not limited to a particular manner, and concatenative synthesis or other well-known techniques may be used.

The healing message is not limited to the one in which a conversation is finished in one-time dialog but may be such an utterance that keeps the conversation. For example, home-appliance system 20 may recognize the utterer's reply and give an utterance including such a question that prompts the next reply as a healing message. More specifically, in general, there are various means for alleviating human tiredness or stress, and the degree of alleviation also varies with people. Home-appliance system 20 therefore may successively output messages that suggest an action that may contribute to alleviation of tiredness or stress. As an example, for the utterer's reply, home-appliance system 20 may successively give such utterances that draw a next reply, such as "Why don't you get some rest?" "Why not take a walk?" "How about a trip?" "How about eating delicious cake?"

In many of the examples above, healing message 1522 is prepared in advance in server 310. In another aspect, message 1522 may be registered in server 310 or home appliance 350 by another information communication terminal. For example, referring to FIG. 2, when the resident of home 210 stays at home 220 at a distance, the family in home 210 may leave a message on provider server 250 or other server 310, or cleaning robot 221 or other appliances provided in home 220, through a smartphone or other information communication terminals. The stayer at home 220 may listen to the family's voice from cleaning robot 221 or others to alleviate tiredness or stress.

Eighth Embodiment

Using Pictures

In the foregoing embodiments, voice is used as a question to the user by home appliance 350. The question to the user is not limited to voice and may be, for example, characters or other images or pictures.

Referring to FIG. 16, another application example of the technical concept will now be described. FIG. 16 is a diagram illustrating an aspect in which television 215 that is home appliance 350 according to an eighth embodiment interacts with a user.

For example, in an aspect A, television 215 is not powered on but on standby. Subsequently, when server 310 determines to start the diagnosis mode, or a predetermined timing has come, television 215 displays such an image or message that asks about the user's condition. Television 215 may additionally display such a message that prompts operation of a remote controller (not shown).

When the user responds to the display on television 215 by operating the remote controller, the response result is transmitted to server 310, and the user's condition is diagnosed. When server 310 determines that the user's mental state is not good, server 310 transmits an instruction to television 215 to display pictures, images, or character information that makes the user laugh. In response to reception of the instruction, television 215 displays such pictures, images, or character information. The user may laugh in spite of himself/herself to see the display, thereby alleviating stress or fatigue.

As described above, with the technical concept according to the present embodiment, home appliance 350 included in home-appliance system 20 asks the user a question by voice or pictures and acquires the user's reply to the question to diagnose the user's mental state. Since home-appliance system 20 outputs voice or picture to the user based on the diagnosis, the fatigue or stress of the user who recognizes the voice or picture may be alleviated.

As is clear from the foregoing description, the definition of housework (=activities in daily life) in the present embodiment is not limited to cleaning, laundry, and cooking. Accordingly, the home appliance in the present embodiment is not limited to home electronic machines in a narrow sense, such as cleaning robots, washing machines, electric rice cookers, air conditioners, and televisions. The home appliance may include, for example, in connection with move, automobiles equipped with navigation systems for supporting drive via linguistic communication, electrically-driven wheelchairs assisting people with difficulties in walking, and power suits for supporting heavy work. In other words, the technical concept according to the present embodiment includes any device that is able to execute the function assisting in daily life through voice, character, image or other linguistic interfaces.

Ninth Embodiment

Although voice or pictures are used for alleviating tiredness or stress in the foregoing examples, tiredness or stress is not necessarily alleviated with voice or pictures alone. Examples of the implementation may include emission of fragrance (that is, aroma), projection of pictures (that is, color), and dancing of the home appliance (that is, motion). More specifically, in another aspect, when home appliance 350 receives the user's reply to an utterance and determines that the user feels stress or fatigue, home appliance 350 may emit fragrance charged in advance. In another aspect, home appliance 350 may have a projector function. In this case, when home appliance 350 receives the user's reply to an utterance and determines that the user feels stress or fatigue, home appliance 350 displays pictures on the ceiling or a side face of the room in which it is installed. Examples of the pictures may include pictures supposed to have a high healing effect and pictures of landscapes of foreign countries.

In yet another aspect, cleaning robot 221 serving as home appliance 350 may move singing when receiving the user's reply to an utterance and determining that the user feels stress or fatigue. The user's fatigue or stress may be alleviated through voice and motion.

The disclosed embodiments above may be configured with one or more modules. The one or more modules may include software modules, hardware modules, and combinations thereof. The software modules include communication programs, application programs, subroutines, and other programs. The hardware modules include processors, memories, circuit elements, monitor devices, motors, speakers, microphones, and other elements.

The embodiment disclosed here should be understood as being illustrative rather than being limitative in all respects. The scope of the present invention is shown not in the foregoing description but in the claims, and it is intended that all modifications that come within the meaning and range of equivalence to the claims are embraced here.

REFERENCE SIGNS LIST

1 CPU, 2 mouse, 3 keyboard, 4 RAM, 5 hard disk, 6 optical disc drive, 7 communication interface, 8 monitor, 9 CD-ROM, 20 home-appliance system, 21 utterance unit, 22 voice input unit, 23 determination unit, 24, 256, 809 storage unit, 25 drive mechanism, 30 the Internet, 40 information communication terminal, 210, 220 home, 211, 221 cleaning robot, 212 router, 213, 223 refrigerator, 214, 224 light, 215, 225 television, 216, 226 air conditioner, 230 medical institution server, 240 local government server, 250 provider server, 251, 311, 351, 801 communication unit, 252, 802 control unit, 253 voice input receiving unit, 254, 316, 811 voice recognition unit, 255 response processing execution instructing unit, 258, 820 utterance content database, 259 state storing unit, 260, 270 smartphone, 280 automobile, 310 server, 312 appliance control signal transmitting unit, 313, 356 appliance control unit, 314, 353 control command receiving unit, 315, 352 overall control unit, 317 dialog control unit, 318 voice synthesis unit, 319 person identifying unit, 320 appliance state utterance generating unit, 321 information utterance generating unit, 322 fatigue assessment utterance generating unit, 323 fatigue assessing unit, 324 assessment notification unit, 325 personal information storing unit, 350 home appliance, 354 state acquiring unit, 355 personal information acquiring unit, 357 voice acquisition control unit, 358 utterance control unit, 359 state display unit, 700 computer, 803 microphone, 804 speaker, 805 cleaning unit, 806 drive unit, 808 display unit, 812 response processing executing unit, 813 operation mode switching unit, 814 voice input accepting unit.

The invention claimed is:

1. An interactive home-appliance system comprising:

a speaker;

a microphone;

a memory area for storing an assessment criterion for assessing stress or fatigue based on conversation with an utterer;

the memory area further storing data for outputting voice alleviating stress or fatigue; and a processor, the processor being configured to:

in response to detection of an event in the interactive home-appliance system, switch an operation mode of the interactive home-appliance system from a normal mode to a diagnosis mode for diagnosing an utterer;

cause the speaker to output a voice for making an inquiry;

determine stress or fatigue of an utterer, based on the assessment criterion and a response of the utterer to the inquiry output from the interactive home-appliance system, in the diagnosis mode; and cause the speaker to output an utterance based on a result of the determination and the data, in the diagnosis mode.

2. The interactive home-appliance system according to claim 1, wherein the utterance from the speaker in the diagnosis mode includes a question to the utterer himself/herself.

3. The interactive home-appliance system according to claim 1, wherein the event includes any of:

an internal event produced inside the interactive home-appliance system;

an appliance control event based on control of the interactive home-appliance system;

an event based on input of voice to the interactive home-appliance system;

that the normal mode continues for a predefined time;

that a predefined time has elapsed since a timing when a previous diagnosis mode is executed;

that a keyword relational to diagnosis from a past dialog is detected in a current utterance; and that an utterance to the interactive home-appliance system is no longer produced.

4. The interactive home-appliance system according to claim 1, wherein the speaker outputs an utterance prompting the utterer to receive a doctor's diagnosis.

5. The interactive home-appliance system according to claim 1, wherein:

the processor is configured to specify an utterer, based on input to the interactive home-appliance system.

6. The interactive home-appliance system according to claim 5, wherein:

the processor is further configured to:

store history of one or more utterers to the interactive home-appliance system, and determine stress or fatigue of the utterers, based on the history.

7. The interactive home-appliance system according to claim 1, wherein:

the processor is further configured to transmit a determination result by the determination module or a dialog situation by the interactive home-appliance system, to an information processing terminal configured to communicate with the interactive home-appliance system.

8. The interactive home-appliance system according to claim 1, further comprising a receiver for receiving information related to a dialog situation with an utterer.

9. The interactive home-appliance system according to claim 1, wherein:

the processor is further configured to accumulate a determination result by the determination module and a dialog situation with an utterer.

10. A server device comprising:

one or more communication interfaces;

one or more memories for storing data and instructions; and one or more processors, connected to the one or more memories, for executing the instructions, when executed by the one or more processors, the one or more processors being configured to;

receive, via the one or more communication interfaces, a signal from an interactive home appliance;

transmit, via the one or more communication interfaces, a signal to the interactive home appliance;

access the one or more memories to read an assessment criterion for assessing stress or fatigue based on conversation with an utterer;

access the one or more memories to read data for outputting voice alleviating stress or fatigue;

switch, in response to detection of an event in the server device, an operation mode of the server device from a normal mode to a diagnosis mode for diagnosing an utterer;

output, via the one or more communication interfaces, a voice signal for making an inquiry;

determine stress or fatigue of an utterer to the interactive home appliance, based on the assessment criterion and a voice signal received as a response to the inquiry from the interactive home appliance, in the diagnosis mode, and transmit, via the one or more communication interfaces, a signal for outputting an utterance based on a result of the determination and the data to the interactive home appliance.

11. The server device according to claim 10, wherein the server device is able to communicate with a plurality of the interactive home appliances, and the one or more processors further configured to generate an utterance corresponding to the interactive home appliance.

12. An interactive home appliance comprising:

a voice output module for outputting voice;

a voice input module configured to accept input of voice; and a drive mechanism responsive to an utterance to the home appliance to perform an operation for providing support in life of an utterer, wherein when a predetermined condition is established for the interactive home appliance and an utterer, an operation mode of the interactive home appliance switches to a diagnosis mode, the voice output module outputs voice asking about a condition of an utterer in order to diagnose the utterer, in the diagnosis mode, and the voice output module is configured to output an utterance for alleviating stress or fatigue, based on a result of determination of stress or fatigue and voice data for alleviating stress or fatigue, the determination of stress or fatigue being performed using an assessment criterion for assessing stress or fatigue based on conversation with the utterer, and the conversation.

13. The interactive home appliance according to claim 12, further comprising:

a transmitting module configured to transmit a signal representing a response content of the utterer to another information communication device; and a receiving module configured to receive an utterance based on a result of the determination performed using the response content, and the data, from the information communication device.

14. A computer-implemented method for allowing a home appliance to interact, comprising:

outputting voice;

accepting input of voice;

switching an operation mode of the interactive home appliance to a diagnosis mode, based on that a predetermined condition is established for the interactive home appliance and an utterer;

outputting voice asking about a condition of an utterer in order to diagnose the utterer, in the diagnosis mode;

accessing an assessment criterion for assessing stress or fatigue based on conversation with an utterer;

accessing data for outputting voice alleviating stress or fatigue;

determining stress or fatigue of an utterer, based on the assessment criterion and a response of the utterer; and outputting an utterance based on a result of the determination and the data.

* * * * *